United States Patent [19]

Litovitz

[11] Patent Number: 5,450,859
[45] Date of Patent: Sep. 19, 1995

[54] PROTECTION OF LIVING SYSTEMS FROM ADVERSE EFFECTS OF ELECTRIC, MAGNETIC AND ELECTROMAGNETIC FIELDS

[75] Inventor: Theodore A. Litovitz, Annapolis, Md.

[73] Assignee: The Catholic University of America, Washington, D.C.

[21] Appl. No.: 88,034

[22] Filed: Jul. 6, 1993

Related U.S. Application Data

[63] Continuation-in-part of Ser. No. 642,417, Jan. 17, 1991.

[51] Int. Cl.⁶ .................................. A61B 19/00
[52] U.S. Cl. .......................... 128/897; 600/9
[58] Field of Search .......................... 600/9–15; 128/897–899

Primary Examiner—Lee S. Cohen
Assistant Examiner—John P. Lacyk
Attorney, Agent, or Firm—Cushman Darby & Cushman

[57] ABSTRACT

The disclosed embodiments of the inventions disclosed in this application develop a 'protection' electric, magnetic or electromagnetic field or fields which are either superimposed upon an ambient field which is detrimental to the health of living systems, or is incorporated into the electrical circuit of the device which is generating the detrimental field. Either arrangement is successful in 'confusing' living cells, and thereby reducing the harmful effects of the otherwise detrimental field.

52 Claims, 22 Drawing Sheets

_Fig. 3a._
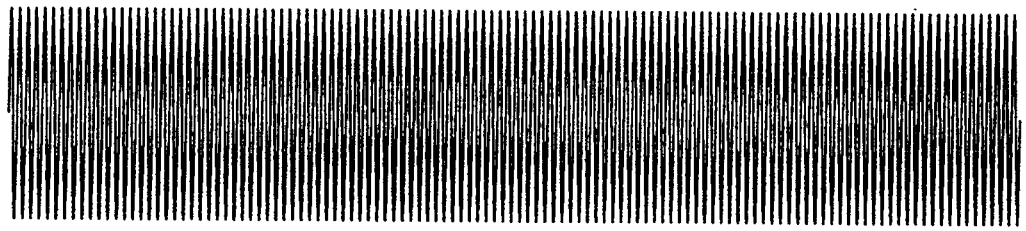
_Fig. 3b._
_Fig. 3c._
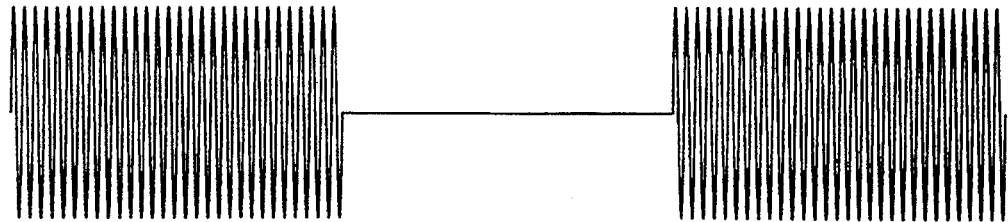

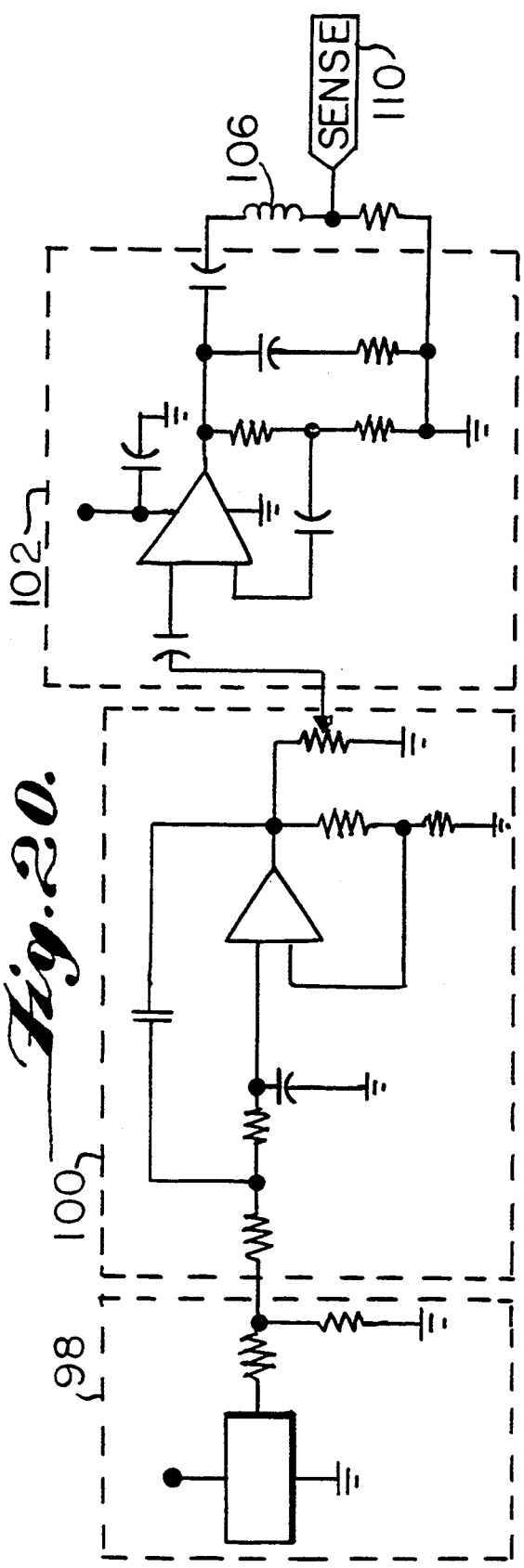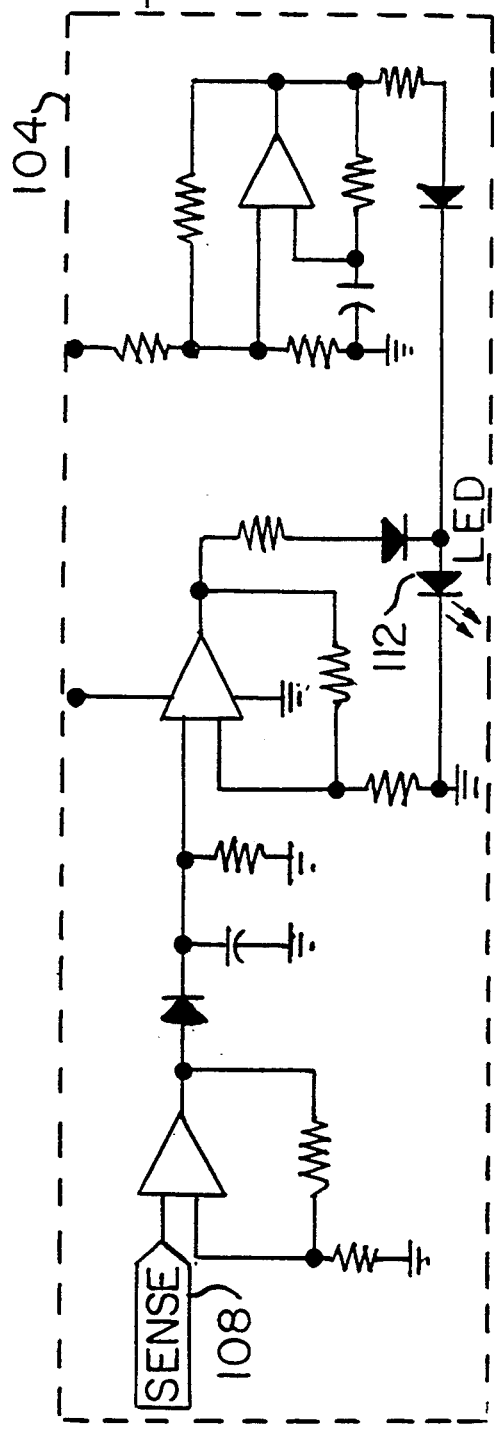
Fig. 20.
Fig. 21.

PROTECTION OF LIVING SYSTEMS FROM ADVERSE EFFECTS OF ELECTRIC, MAGNETIC AND ELECTROMAGNETIC FIELDS

CROSS-REFERENCE TO RELATED APPLICATION

This application is a Continuation-In-Part of co-pending application Ser. No. 07/642,417, filed Jan. 17, 1991, the subject matter of which is incorporated herein.

BACKGROUND OF THE INVENTION

1. Field of the Invention

The inventions described herein relate in general to arrangements (apparatus and methods) for protecting living systems from the adverse effects upon them of electric fields, magnetic fields, and electromagnetic fields. In some instances hereinafter, electric fields, magnetic fields, and electromagnetic fields will all jointly be referred to simply as fields.

More specifically, the inventions are directed to electrical, electronic, electromechanical, and electromagnetic devices, systems, and installations and the effect of their concomitant fields on people, animals, and other living systems. The inventions a non-desired and potentially bioeffecting ambient field into a harmless non-bioeffecting field by either superimposing on the ambient field a 'protection' field which sanitizes the ambient field, or changing the electrical operation of the device which is producing the ambient field so that its field emissions become less harmful. Both arrangements are successful in 'confusing' the living cell or cells, thereby reducing the potentially harmful effects of the ambient field.

This application incorporates the subject matter set forth in two appendicies, filed herewith entitled: EVIDENCE THAT BIOEFFECTS CAN BE CAUSED BY WEAK ELECTROMAGNETIC FIELDS and A SUMMARY OF DATA DEMONSTRATING THE FACT THAT PROPERLY FLUCTUATING ELECTROMAGNETIC FIELDS CAN BLOCK THE BIOEFFECT OF COHERENT STEADY STATE EM FIELDS. 2. Description of Related Art For some years there has been a growing recognition and concern that humans are suffering adverse effects, notably cancers, from living and/or working in ambient electromagnetic fields, particularly those fields which are alternating or pulsating at extremely low frequencies, or being modulated at extremely low frequencies. Extremely low frequencies, hereinafter referred to as ELF, are frequencies of the order of 1000 Hz and below. Ambient frequencies particularly identified with an enhanced risk of cancer are power line frequencies, which are 60 Hz in the U.S. and 50 Hz in the U.K., European Continental countries, and elsewhere. Electromagnetic fields existing near devices using cathode ray tubes also are implicated, due to fields generated by the magnetic electron beam deflecting devices included in tube control apparatus.

Various articles have been published on the electromagnetic field problem. Over the past 14 years a series of epidemiological studies have found that low level electromagnetic fields [even as low as 1 $\mu$T (1 micro Tesla) produced by 60 Hz power lines can be correlated with increased incidence of certain diseases. The correlation is strongest for those who have lived or worked in this environment for many years. For example, an increased risk of cancer has been found among children who lived for several years close to power distribution lines [Wertheimer, N. and Leeper, E. "Electrical Wiring Configurations and Childhood Cancer" AM J EPIDEMIOLOGY, 109, 273–284 (1979); also, Savits, D. A. et al., "Case Control Study of Childhood Cancer and Exposure to 60-Hertz Magnetic Fields, " AM J EPIDEMIOLOGY, 128, 10–20 (1988); also London, D. A. et al. "Exposure To Electric and Magnetic Fields And Risk of Childhood Leukemia", AM. J. EPIDEMIOLOGY, 135, 1069–1070 (1992); also, Milham, S. Jr., "Increased Mortality in Amateur radio Operators Due to Lymphatic and Hematopoietic Malignancies," AM. J. EPIDEMIOLOGY, 128, 1175–1176 (1988).

The research indicates that children from high electromagnetic field exposure homes have a 50 percent greater risk of developing cancer, particularly leukemia, lymphomas, and nervous system tumors. Other data also show that men working in electrical jobs, such as electricians and telephone lineman are at higher risk for brain tumors and other cancers. In a recent study in the Los Angeles area, S. Preston-Martin and collaborators at the University of Southern California found that men who had worked for 10 Years or more in a variety of electrical occupations had a ten times greater chance of getting brain tumors than men in the control group. [Preston-Martin, S., and Mack, W. and Peters, Jr. "Astrocytoma Risk Related to Job Exposure to Electric and Magnetic Fields," presented at DOE contractors Annual Review, Denver Colorado, Nov. 5–8, 1990.]

A study performed by G. Matanoski of Johns Hopkins University found a dose response relationship for cancers in male New York Telephone employees from 1976 to 1980. [Matanoski, G., Elliot, E. and Breysse, P. Poster presented at the annual DOE/EPRI Contractors Review of Biological Effects from Electric and Magnetic Fields, November 1989, Portland, Ore.] Matanoski measured the average magnetic field exposure among different types of employees including installation and repair workers. A comparison of the cancer rates among the various types of employees showed that cable splicers were nearly twice as likely to develop cancer as those employees who did not work on telephone lines. Among central office workers those who were exposed to the fields of telephone switching equipment the rates of occurrence of cancers were unusually high, although not as high as for cable splicers. The central office workers were more than three times as likely to get prostate cancer and more than twice as likely to get oral cancer as co-workers who were less exposed. There were two cases of male breast cancer, a disease so rare that no cases at all would be expected.

The 60 Hz electromagnetic fields found in residential settings can vary from about 0.05 $\mu$T to over 1000 $\mu$T. In-vitro experiments have definitely shown that changes in biological cell function can occur in fields as low or lower than 1 $\mu$T and as high as 500 $\mu$T. R. Goodman and collaborators [Goodman, R. and Henderson, A., "Sine Waves Enhance Cellular transcription," BIOELECTROMAGNETICS, 7, 23–29, 1986)]have shown that RNA levels can be increased by electromagnetic fields ranging in frequency from 15 to 4400 Hz with amplitudes of 18 to 1150 $\mu$T. They have shown that the RNA levels can be enhanced by factors of ten or more. Jutilainen and coworkers [Jutilainen, J., Laara, E. and Saali, K., INT>J. RADIAT. BIOL., 52,787–793, (1987)] have shown that 1 $\mu$T 50-Hertz electromagnetic fields can induce abnormalities in chick embryos. Thus, electromagnetic fields appear not only to be carcinogenic, but also capable of inducing birth defects. Pollack and collaborators, C. T. Brighton, E. O'Keefe, S. R. Pollack and C. C. Clark, J. ORTH. RES. (to be published), have shown that electric fields as low as 0.1 mv/cm at 60 Khz can stimulate growth of bone osteoblasts. McLeod and collaborators have found that in the region between 1 Hz and 100 Hz, much lower fields are needed to stimulate fibroblast growth than at frequencies above and below this range [McLeod, K. J., Lee, R. and Ehrlich, H., "Frequency Dependence of Electric Field Modulation of Fibroblast Protein Synthesis," SCIENCE, 250, 1465 (1987)].

Other than epidemiologic studies, whole body research on EMF exposure has generally been limited to animals. Adverse effects from electromagnetic field exposure have also been shown demonstrated in this case. For example McLean et al. have presented a paper at the Thirteenth Annual Meeting of the Electromagnetic Society, in June 1991 entitled "Tumor Co-promotion in the mouse skin by 60-Hz Magnetic Fields". They have shown that the number of tumors present is increased by the presence of the magnetic field. Frolen et al. in a paper presented to the First European Congress on Bioelectromagnetism in 1991 entitled "Effects of Pulsed Magnetic Fields on the Developing Mouse Embryo". They show that mice exposed to magnetic fields have significantly more fetal resorptions than those which are unexposed. Since the present inventions negate all electromagnetic field induced bioeffects, all living systems can benefit from its application.

One method typically employed in the prior art to protect living systems from the detrimental effects of fields is to shield the field source. The shielding collects the energy of the field, and then typically grounds it. In practice shielding is impractical because it must completely cover a field source in order to contain the field. The field will radiate through any openings in the shield. In reality, devices cannot be entirely shielded, therefore, while the shielding method can reduce the field it does not entirely eliminate it or its potentially hazardous attributes.

Cathode ray tubes (CRT) are a source of electromagnetic fields to which people are often exposed, for instance television sets and computer screens. Attempts have been made by others in the art to shield the field which emanates from CRT's. One type of shield has been devised to surround the electromagnetic coils of the CRT. Another type of shield has been designed to entirely enclose the CRT. The shields which surround the coils do not, however, eliminate the field completely, nor do the shields which entirely enclose the CRT. These methods are often prohibitively expensive and often do not offer complete elimination of the detrimental effect of the fields.

Another method typically used in the prior art to protect living systems from electromagnetic fields is to balance the field from the source so that the source effectively cancels its own field, thus ideally producing no offending field. For instance, the AC power distribution to homes and industries is typically carried over unshielded bare copper wires, suspended in the air from towers. These lines are usually either two-phase or three-phase. Theoretically these lines can be arranged physically and by phase such that the EMF fields produced by the individual lines are each canceled by the other power line(s). In practice, however, this power cancellation is not complete and an ambient field still results. Also, the costs involved to produce a power distribution system such as this is prohibitively high.

The present inventions have many advantages over the methods employed thus far in the art. Many of the embodiments of the inventions are very inexpensive, they can provide positive protection for the individual, and they can be provided at the control of the individual. There is no need to wait until the power company changes the design of its power distribution system, or wait until the television or computer manufacturer completely shields the product. Some of the embodiments of the inventions enable living systems to have individual protection from the detrimental effects of ambient fields, if and when it is desired. Shielding is not always practical, and even when it is practical it is not always complete. Therefore the present inventions can also provide the user with personal control over the detrimental effects of ambient fields.

To the best of my knowledge, to date no one has heretofore proposed my inventions, although over 12 years have lapsed since the first recognition of the dangers of chronic electromagnetic field exposures to humans. There have been many teachings about the use of electromagnetic fields to treat humans for pre-existing diseases or conditions. For example, U.S. Pat. No. 4,066,065 (Kraus 1978) describes a coil structure to create a magnetic field for treatment of a hip joint. U.S. Pat. No. 4,105,017 (Ryaby 1978) describes a surgically non-invasive method of an apparatus for altering the growth, repair or maintenance behavior of living tissues by inducing voltages and concomitant current pulses. U.K. Patent GB 2 188 238 A (Nenov et al. 1986) describes an apparatus alleged to provide analgesic, trophic and anti-inflammatory effects. Costa (1987) U.S. Pat. No. 4,665,898 describes a magnetic coil apparatus for treatment of malignant cells with little damage to normal tissue. An apparatus for treatment of diseases of the peripheral and autonomic nervous system as well as other diseases has been described by Solov'eva et al. ("'Polyus-1' Apparatus for Low-Frequency Magnetotherapy," G. Solor'eva, V. Eremin and R. Gorzon, BIOMEDICAL ENGINEERING (Trans. of: Med. Tekh, (USSR)), Vol. 7, No. 5, pp. 291-1 (1973).

The above procedures are usually referred to as "magnetotherapeutic" procedures. My inventions focus instead on the prevention of disease caused by long term exposure to ambient time varying electric, magnetic and electromagnetic fields. To date, no other proposals have been presented which utilize modifications of the time dependence of the ambient fields to prevent adverse health effects of ambient electromagnetic fields. Basic to all the patents and articles which describe the treatment of pre-existing diseases by electromagnetic fields (magnetic therapy) is the assumption that electric or magnetic fields (often of large magnitude, e.g. 1 to 100 micro Tesla (Ryaby 1978), if applied for some limited period of time, can beneficially alter the functioning of the cells and tissues within living systems. Now it is known that chronic, long term exposure to even very low level, time varying fields (e.g., magnetic fields as low as 0.5 $\mu T$) can cause some of the very diseases which short term therapeutic doses of these fields are used to treat. Methods of protection from the biological effects of magnetic fields have been sorely needed. To find this protection it was necessary for me to recognize that magnetic therapy is carried out by affecting biologic cell function. It had to be realized that if magnetic therapy does not affect the physiological functioning of the living system then no therapeutic effect could result. What was needed, which the present inventions provide, is a method of modifying the ambient fields in which living systems exist in such a way that they have no effect on cell function. This modified field has no utility in the treatment of any disease or biologic malfunction. This modified field is not of any use in magnetic therapy. However, this modified field (because it does not affect the function of the cells and tissues of the living system) has no adverse health effects. Thus, long term exposure to these modified fields will be safe. These modified fields would not, for example, increase the risk of developing cancer.

However, none of the above authors, or anyone else before me, had discovered that periodically changing these very low ambient fields as described elsewhere herein can prevent harmful effects of electromagnetic fields.

SUMMARY OF THE INVENTION

I have concluded that the aforesaid adverse health effects upon living systems (including but not limited to single cells, tissues, animals and humans) may be inhibited by changing in time one or more of the characteristic parameters of the ambient time varying electric, magnetic or electromagnetic field to which the living system is exposed. This may be done in a number of ways, for example, by changes in one or more of frequency (period), amplitude, phase, direction in space and wave form of the field to which the living system is exposed. As for the time period between changes, I have concluded that these time periods should be less than approximately ten (10) seconds, and preferably should not exceed approximately one (1) second. The changes may occur at regular or irregular intervals. If the changes occur at regular intervals the shortest time between changes should be one-tenth (0.1) second or greater. If the changes occur at irregular random intervals the time between changes can be shorter. These changes can be accomplished by superimposing these special time-dependent fields upon the ambient field, or by changing with time the characteristic parameters of the original fields.

The change or changes in the ambient field frequency should be about 10 percent or more of the related characteristic parameters of the field before the change My proposal to protect living systems from the adverse effects of electric, magnetic or electromagnetic fields by creating special ambient fields as aforesaid is based on my conclusion that something must be done to confuse the biologic cell so that it can no longer respond to the usual fields found in the home and work place. I have discovered that the fluctuating fields mentioned above will prevent the adverse effects of the usual environmental fields. As above stated, these fluctuations can occur either in the amplitude, frequency (period), phase, wave form or direction-in-space of the newly created "confusion" field.

To affect cell function some insult (e.g. drug, chemical, virus, electromagnetic field, etc.) will cause a signal to be sent from receptors (often at the cell membrane) into the biochemical pathways of the cell. Although the exact receptor and signalling mechanism utilized by the cell to recognize the fields is not known, I have discovered that the mechanism of detection of electric, magnetic or electromagnetic fields can be stopped by confusing the cell with fields that vary in time in the ways specified herein.

For example, a 60 Hz electromagnetic field having a magnetic component of 10 $\mu$T can cause a two fold enhancement of the enzyme ornithine decarboxylase. If this field is abruptly changed in frequency, amplitude, wave form, direction or phase at intervals of more than 10 seconds, the two fold enhancement persists. If, however, the frequency, amplitude or waveform parameters are changed at approximately 1 second intervals, the electromagnetic field has no effect. The cell does not respond because it has become confused. Similar electric fields in tissue with amplitudes ranging from 0.1 to 50 $\mu$v/cm. can be useful in protecting the living system from adverse effects. To create these fields within a living system at 60 Hz the field strength outside the living systems must be about one million times larger (i.e. 0.1 to 50 v/cm.)

I consider that my inventions function best with ambient fields having an electric component of 50 Kv/M or less and/or a magnetic component of 5000 $\mu$T or less. As for lesser field strengths, electric components of 0.5 Kv/M and/or magnetic components of 5 $\mu$T are exemplary. Good results are obtained when the confusion field is generated by interruption of a coherent signal (e.g. a 60 Hz sinusoidal wave) and the frequency of this signal is similar (but not necessarily equal) to the fundamental frequency of the ambient field. However, when protecting against the effects of modulated RF or modulated microwave fields the confusion field can be effective if it contains only frequency components similar (but not necessarily equal) to those of the modulation. The rms amplitude of the confusion field should preferably be approximately the same or larger than that of the ambient field.

The time between changes in properties such as frequency, phase, direction, waveform or amplitude should be less than 5 seconds for partial inhibition of adverse effects but preferably between one tenth (0.1) second and one (1) second for much more complete protection. When the time between changes is irregular and random (e.g. a noise signal) the time between changes can be less than one tenth (0.1) second. For example I have found that complete inhibition can be achieved with a noise signal whose rms value is set equal to the rms value of the ambient signal and whose bandwidth extends from thirty (30) to ninety (90) hertz.

It is preferred to have the field to which the living system is exposed be my confusion field for the duration of the exposure. However, benefit will be achieved if my confusion field is in existence for only a major portion of the total exposure time.

I have referred above to electric, magnetic and electromagnetic fields because, insofar as they are distinct, ambient fields of each type are capable of causing harm to living systems, but if changed according to my inventions will inhibit the on-set of adverse effects.

I have confirmed the operability of my inventions by several observations and procedures. One observation has been the effect of coherence time (defined herein as the time interval between changes of the characteristic parameters of the fields) of the applied field on bioelectromagnetic enhancement of ornithine decarboxylase (ODC) specific activity. ODC has been found to be intimately linked to the process of cell transformation and tumor growth.

Specific activities of this highly inducible enzyme were examined following mammalian cell culture exposure to electromagnetic fields. Monolayer cultures of logarithmically growing L929 cells were exposed to fields alternating between 55 and 65 Hz. The magnetic field strength was 1 μT peak. The cells were exposed to the fields for four hours. The time intervals between frequency shifts varied from 1 to 50 seconds. See Table 1.

TABLE 1

Role of Time Intervals Between Frequency Chances on the Effectiveness of Electromagnetic Exposure in Modifying ODC Activity Ratio of ODC activity in Exposed Compared to unexposed cells

| | Time interval between frequency changes (seconds) | | | | |
|---|---|---|---|---|---|
| | 0.1 | 1 | 5 | 10 | 50 |
| ELF (55 to 65 Hz) | — | 1 | 1.4 | 1.9 | 2.3 |
| Microwaves (modulated alternatively by 55 and 65 Hz) | 1 | 1 | 1.5 | 2.1 | 2.1 |

It can be seen from Table 1, (1), that when the time intervals between frequency shifts in the electromagnetic fields were 10 seconds or greater, the electromagnetic field exposure resulted in a two-fold increase in ODC activity. When the time intervals between frequency shifts (i.e. between 55 Hz and 65 Hz) were shortened to less than 10 seconds, the effectiveness of these ELF (extremely low frequency) fields in increasing ODC activity diminished. At 1 second and below the field has no effect at all (i.e., the activity of the exposed mammalian cells was the same as for unexposed cells). Thus we see that introducing changes in parameters of the electromagnetic field at short enough time intervals prevents any action of the field on cell function.

This finding applies to electromagnetic frequencies as high as the microwave region. Similar data were obtained using 0.9 GHz microwaves modulated at frequencies changing between 55 and 65 Hz at intervals of time ranging from 0.1 to 50 seconds. A 23 percent amplitude modulation was used and the specific absorption rate was 3 mW/g. As can be seen in table 1, when the time interval was 10 seconds or greater, this microwave field also caused a two-fold increase in ODC activity. At shorter time intervals the effect of the field on ODC activity diminished. When the time intervals between changes were one second or less, the field had no effect on ODC activity.

To further demonstrate the protective effect of my confusion fields, I studied the effects of modulation on the ability of exogenous electromagnetic fields to act as a teratogen and cause abnormalities in chick embryos. In experimental methods now described, I modulated the amplitude of a 60 Hz electromagnetic field. Fertilized White Leghorn eggs were obtained from Truslow Farms of Chestertown, Md. These were placed between a set of Helmholtz coils inside an incubator kept at 37.5° C. During the first 48 hours of incubation one group of eggs was exposed to a 60 Hz continuous wave (cw) sinusoidal electromagnetic field whose amplitude was 1 μT. Another group was exposed to a 60 Hz cw sinusoidal electromagnetic field whose amplitude was 4 μT. Another group of eggs was exposed to a 60 Hz sinusoidal electromagnetic field whose amplitude was varied from 1.5 to 2.5 μT at 1 second intervals. Control eggs were simply placed in the incubator and not exposed to an electromagnetic field. After 48 hours of incubation the embryos were removed from their shells and examined histologically. It was found that the control group (not exposed to the 60 Hz magnetic field) exhibited about 8 percent abnormalities. The embryo groups exposed to 1 μT and 4 μT fields had a higher abnormality rate (14 percent) than the controls indicating that these fields had indeed induced abnormalities. Those embryos exposed to the fields modulated at 1 second intervals had an abnormality rate the same as the unexposed eggs. Thus the 1 second modulation (or coherence time) effectively eliminated the teratogenic effect of the magnetic field.

When an ambient field is present (such as 60 Hz field from a power line or electrical appliance) which can not be directly modulated, a confusion field must be superimposed upon the ambient field. I studied this superposition effect in several different types of experiments.

As in the experiments above the ornithine decarboxylase levels were measured in L929 cells which were exposed to a steady state 10 μT, 60 Hz field. They displayed a doubling of ornithine decarboxylase activity after 4 hours of exposure. The exposure was repeated with the simultaneous application of a) a 10 μT 60 Hz magnetic field and b) a random EM (noise) magnetic field of bandwidth 30 to 90 Hz whose rms value was set equal to that of the 60 Hz field and whose direction was the same as that of the 60 Hz field. Under these conditions no statistically significant enhancement of the ornithine decarboxylase activity was observed. As the rms noise amplitude was lowered, increased values of EMF induced ornithine decarboxylase activity were observed. This can be seen in Table 2.

TABLE 2

Effect of EM noise on 60 Hz EMF enhancement of ODC activity in L929 murine cells

| Noise Amplitude rms (μT) | Signal/Noise [signal = 60 Hz] | Percent of 60 Hz Induced Enhancement |
|---|---|---|
| 0 | ∞ | 100 ± 10 |
| 0.5 | 20 | 84 ± 12 |
| 1.0 | 10 | 50 ± 10 |
| 2.0 | 5 | 36 ± 7 |
| 5.0 | 2 | 8 ± 11 |
| 10.0 | 1 | 1 ± 8 |

It can be seen from Table 2 that when the noise is about equal to the signal (the 60 Hz field) no biomagnetic effect occurs, but as the rms noise amplitude is lowered less protection is afforded by the noise field.

To demonstrate that the confusion field can be perpendicular to the ambient field and still offer protection the ODC experiment using L929 murine cells was repeated again using 60 Hz, 10 μT as the stimulating ambient field, but this time the confusion field was generated by coils aligned perpendicular to the coils generating the ambient magnetic field. The confusion field this time was a 60 Hz field whose amplitude changed from 5 μT to 15 μT at 1 second intervals. No enhancement of the ODC activity was observed under these conditions. The ratio of exposed ODC activity to control ODC activity was found to be 1.03±0.08. Thus even when the confusion field is perpendicular to the ambient field full protection against adverse effects can be achieved.

If one wishes to render harmless the magnetic fields of heating devices such as electric blankets, heating pads, curling irons, or ceiling cable heat sources for the home, the parameters of the current being delivered to these devices should be changed at intervals less than 10 seconds, or preferably at intervals less than 1 second. One method is to turn the current on and off for consecutive 1 second intervals. However this would render the heat source inefficient since it could only deliver half the average power for which the device is designed. In order to improve the efficiency I have shown that when a 60 Hz field is on for a time greater than when it is off it can still confuse the cell and no bioresponse will occur. The on time should still be preferably on the order of 1 second. However the off time should not be less than 0.1 seconds for full protection. Listed in Table 3 are the results of ODC experiments using L929 murine cells of the type described above. A 10 μT 60 Hz field was applied to the cells. The field was interrupted every second for varying time durations. It can be seen that even with off times as short as 0.1 seconds the cell is confused and no enhancement of ODC activity occurs. As the off time decreases below 0.1 seconds the cell begins to respond to the magnetic field. For off times as low as 0.05 seconds about 70% of full response occurs. It is clear that the preferable range for off times is from about 0.1 to about 1.0 seconds.

TABLE 3

Effect of Interruption Time on 60 Hz EM Field Enhancement of ODC Activity in L929 Murine Cells

| Off Time (seconds) | On Time (seconds) | Percent of 60 Hz Induced Enhancement |
|---|---|---|
| 0.1 | 1 | 3 ± 9 |
| 0.05 | 0.95 | 33 ± 3 |
| 0.025 | 0.975 | 70 ± 17 |

From these experiments we see that a device which interrupts the current in heating applications can be at least 90% efficient in terms of utilizing the full capabilities of the heating system, while at the same time providing a bioprotective confusion field.

As described above there is considerable epidemiological evidence that children living near power lines have a significantly higher rate of incidence of childhood leukemia. One method of rendering these fields harmless is to create a fluctuating field by stringing on the poles a pair of wires shorted at one end and connected to a low voltage current source at the other end. The current should fluctuate at the proper intervals (e.g. approximately one second intervals would be quite effective). Because in this case one is often interested in using as little power as possible short duty cycles would be an efficient power saving strategy. For example we have shown that in the experiment described above and reported in Table 3 the effect of 60 Hz exposure on the ODC activity in L929 cells can be mitigated by superimposing a 60 Hz field of equal peak value but which is on for 0.1 s and off for 0.9 s. Thus we save a factor of ten in power in this application relative to the one second on, one second off, regime.

According to my inventions, there are many different arrangements for converting an otherwise harmful field into a non-harmful one. Some of these are as follows:

One embodiment is to create a confusion field in a living space by placing several time dependent grounding devices on metal plumbing pipes. These devices cause fluctuating paths for electric current in plumbing pipe and therefore fluctuating fields in any room in the house or other human or animal-occupied structure.

Another embodiment is to change an otherwise harmful field into a non-harmful one by inserting fluctuating resistance paths in series with heating devices such as electric blankets.

Another embodiment is to create a confusion field by placing devices near appliances which generate harmful field to create fluctuating electromagnetic fields near the appliances. The confusion field is superimposed onto the uncontrolled source of the original harmful field.

Another embodiment is to eliminate the hazards created by the field in the region around electric devices by modulating the electric current flowing or voltage across the device. The modulation can be controlled by means which are external or internal to the device.

Another embodiment is to eliminate the hazards created by the field in the region around electric devices, by modulating the electromagnetic field around the device. This modulation can be caused by means which are external or internal to the device.

Another embodiment is to eliminate the hazards created by the field in the region surrounding electric heating devices, such as electric blankets, heating pads, and electrically heated water beds, by modulating the current and/or voltage in the device. This modulation can be caused by means which are external or internal to the device.

Another embodiment is to eliminate the hazards created by the field in the region around electric power distribution systems by superimposing a modulated electromagnetic field in the region of space to be protected.

Another embodiment is to eliminate hazards created by the electromagnetic fields in the region around the metallic plumbing used to ground electrical lines by superimposing a modulated electromagnetic field in the region of space to be protected. This can be done by passing modulated currents through the plumbing itself or by passing modulated currents through external circuits.

Another embodiment is to eliminate hazards created by the field around cathode ray tube devices such as video display terminals and television sets by superimposing a modulated electromagnetic field. The source of this modulated electromagnetic field can be placed either inside or outside the cathode ray tube device.

Another embodiment is to eliminate hazards created by the field in the region around a microwave oven by superimposing a modulated electromagnetic field in the region of space to be protected.

Another embodiment is to eliminate the hazards created by the field in the region surrounding electrical power lines.

Clearly many of the above procedures may be adapted to protect laboratories, industrial plants, etc., wherein cells not in humans or in multi-cell living systems may exist.

BRIEF DESCRIPTION OF THE DRAWINGS

I will next describe various techniques and apparatus for carrying out my invention. These descriptions will be aided by reference to the accompanying drawings, in which:

FIGS. 3a, 3b and 3c provide a representation of the effect of direct modulation on a 60 Hz sine wave using square wave modulation.

FIG. 20 is a circuit diagram of an implementation of a bioprotected hair dryer.

FIG. 21 is a circuit diagram of a detection system to detect the presence of a bioprotective field.

DETAILED DESCRIPTION OF THE PREFERRED EMBODIMENTS

Figure 1:
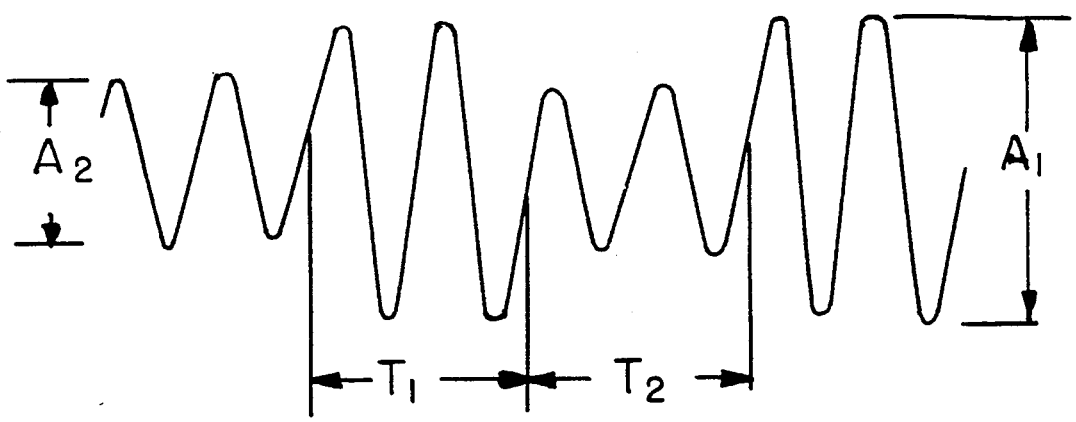
FIG. 1 is a plot of amplitude vs. time of a sinusoidal function modulated as to amplitude.
Figure 2:
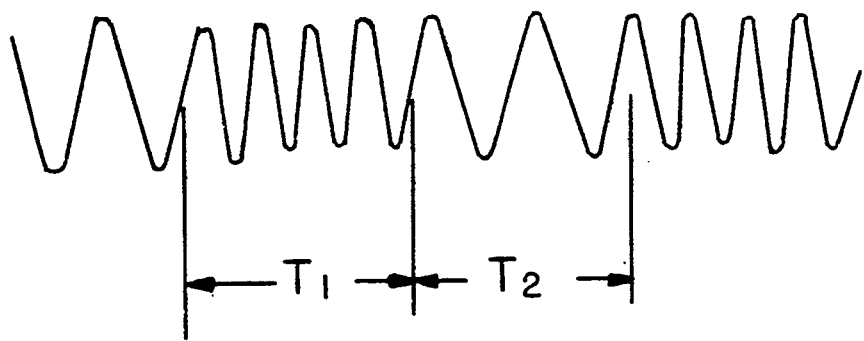
FIG. 2 is a plot of amplitude vs. time of a sinusoidal function modulated as to frequency.

Any voltage, current, electric field, magnetic field, or electromagnetic field which varies repetitively in time can be described by its waveform, peak amplitude (A), frequency (period), direction and phase. Modulation of the wave refers to the time dependent variation of any of these parameters. For example, pulse modulation of the amplitude of any of the parameters refers to a change in amplitude. Two examples of this modulation are shown in FIGS. 1 and 2. In FIG. 1 the amplitude is modulated by a pulse. Thus, for a period of time, $T_1$, the amplitude of the sinusoidally varying voltage is $A_1$. For a second time period, $T_2$, the amplitude is $A_1$. The values of $T_1$ and $T_2$ need not be equal but they must each be about 1 second or less for best results. Many variations in the modulation of a time varying voltage can be used, such as a sinusoidal modulation of the original sine wave. Thus, a 60 Hz sine voltage could be amplitude modulated by a 1 Hz sinusoidal variation. Another possibility is a saw tooth variation in the amplitude of a 60 Hz sine voltage. In all of the possible modulated fields, at least one of the parameters, such as amplitude, waveform, phase, direction or frequency must not be constant for a time duration of more than about 1 second.

Thus, for example, in FIGS. 1 and 2 the values of $T_1$ and $T_2$ must not be longer than about 1 second. For best results, $A_1$ should be greater than $1.2A_2$, and preferably greater than $2A_2$.

Whenever a microwave field is being modulated at a frequency of 100,000 Hz or less, steps should be taken to achieve protection according to my inventions by periodic parameter changing as described herein.

Another method of modulating the detrimental field is by using square wave modulation. That is, interrupt the power delivered at a regular interval. The modulation frequency should be preferably of the order of one second, as guided by the Litovitz invention. The interruption time should be preferably between 0.1 and 0.9 seconds, corresponding to a duty cycle between 10% and 90%. FIG. 3 depicts the method of square wave modulation of a sinusoidal waveform.

Figure 3D:
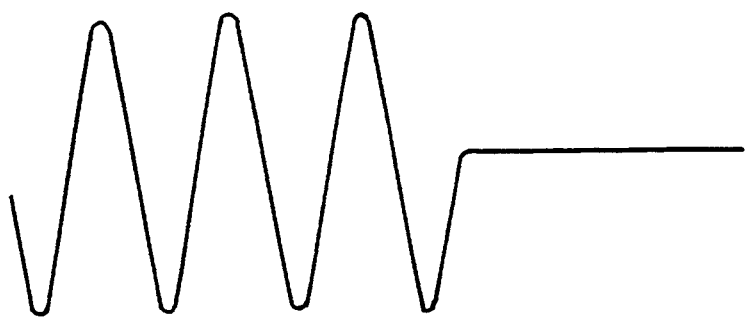
FIG. 3d is an enlarged view of the signal of FIG. 3c at the point at which it is switched.

Referring to FIG. 3a, a sinusoidal signal is depicted. FIG. 3b depicts the controlling sequence to the sinusoidal signal of FIG. 3a using this method, and FIG. 3c is the resulting bioprotected sinusoidal signal. FIG. 3d is an enlarged view of the signal of FIG. 3c at the point at which it is switched.

Another method of modulating the detrimental field is by using DC biased square wave modulation. That is, reduce the power delivered at a regular interval. The modulation frequency and the interval for amplitude reduction should vary in accordance with this specification. Power reduction should be preferably of the order of 50%. FIG. 4 depicts the method of modulation of a sinusoidal waveform by a DC biased square wave.

Figure 4A:
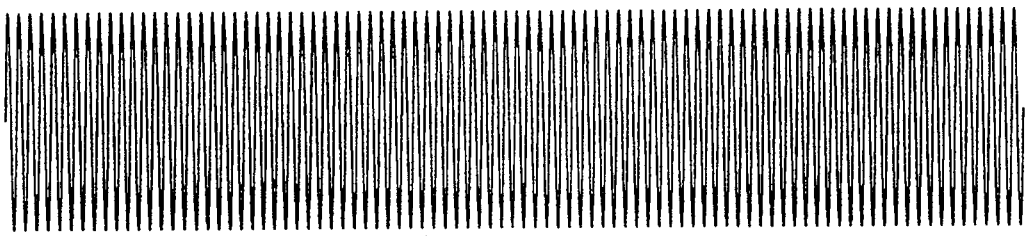
FIGS. 4a, 4b, and 4c provide a representation of the effect of direct modulation of a 60 Hz sine wave using DC biased square wave modulation.
Figure 4B:
Figure 4C:
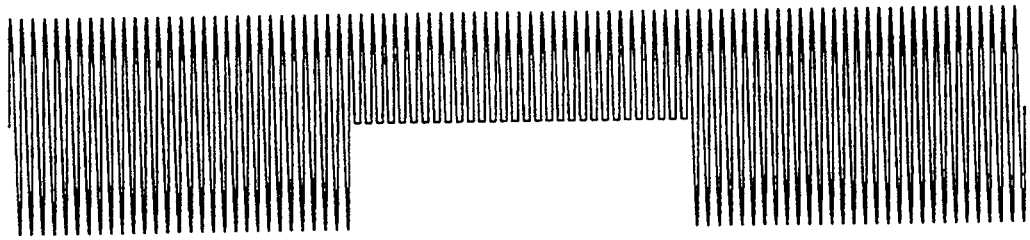
Figure 4D:
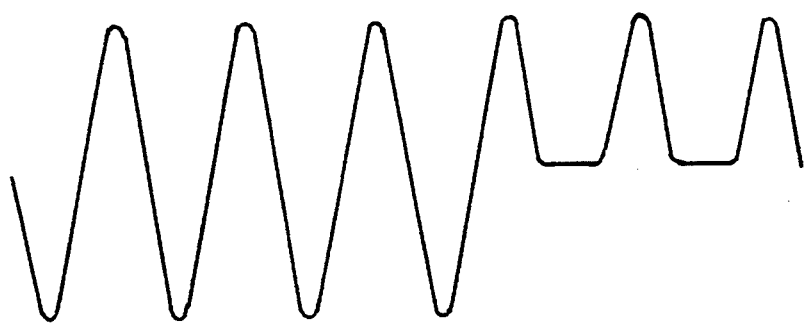
FIG. 4d is an enlarged view of the signal of FIG. 4c at the point at which it is switched.

Referring to FIG. 4a, a sinusoidal signal is depicted. FIG. 4b depicts the controlling sequence to the sinusoidal signal of FIG. 4a using this method, and FIG. 4c is the resulting bioprotected sinusoidal signal. FIG. 4d is an enlarged view of the signal of FIG. 4c at the point at which it is switched.

Another method of modulation of the detrimental field is by using frequency modulation of a square wave periodic signal. That is, change the frequency of the power delivered at a regular interval. The period and duty cycle should be in accordance with this specification. The frequency change should be preferably of the order of 20%.

Another method of modulation of the detrimental field is by using phase modulation of a square wave periodic signal. That is, change the phase of the power delivered at a regular interval. The period and duty cycle should be in accordance with this specification. The phase change should preferably be a multiple of 90 degrees.

Another method of modulation of the detrimental field is by periodically changing the waveform of the detrimental field. The period and duty cycle should be in accordance with this specification. The wave shape change can be for example by full wave rectification. FIG. 5 shows the effect of modulation by periodically changing the waveform by full wave rectification of a sinusoidal waveform.

Figure 5A:
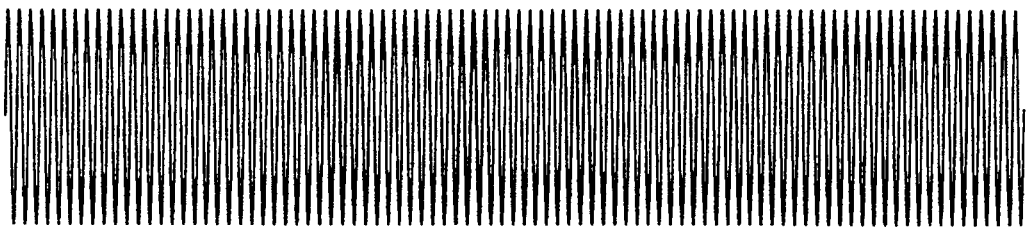
FIGS. 5a, 5b, and 5c provide a representation of the effect of direct modulation of a 60 Hz sine wave using a periodically changed waveform.
Figure 5B:
Figure 5C:
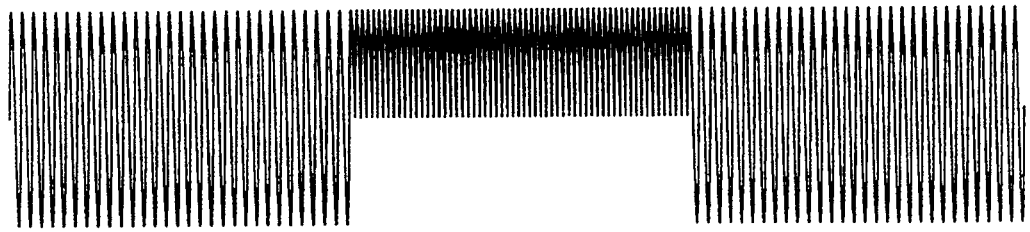
Figure 5D:
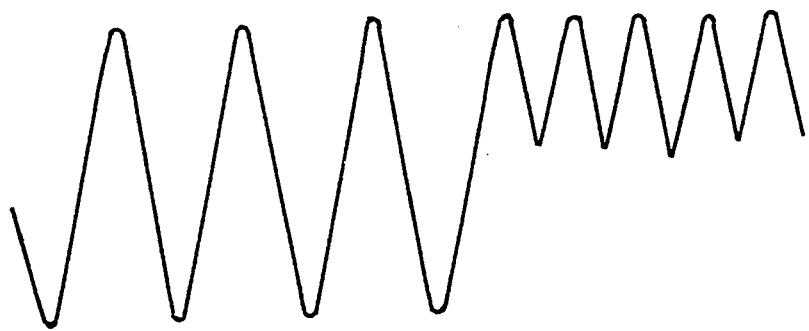
FIG. 5d is an enlarged view of the signal of FIG. 5c at the point at which it is switched.

Referring to FIG. 5a, a sinusoidal signal is depicted. FIG. 5b depicts the controlling sequence to the sinusoidal signal of FIG. 5a using this method, and FIG. 5c is the resulting bioprotected sinusoidal signal. FIG. 5d is an enlarged view of the signal of FIG. 5c at the point at which it is switched.

Another method of modulation of the detrimental field is by changing the detrimental field according to the superposition of a band-limited noise signal with a pass band preferably in the range below 1000 Hz.

When a superposition field source is used, the interference signal may be produced by appropriate modulation of coherent AC signals, or by generation of noise. FIG. 6 shows the effect of the modulation of a sinusoidal waveform by superposition of a band-limited random noise signal.

Figure 6A:
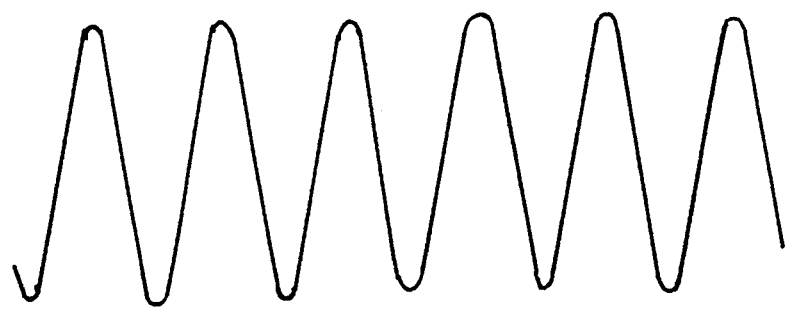
FIGS. 6a, 6b, and 6c provide a representation of the effect of superimposing a band limited noise signal over a sinusoidal signal whose frequency is within the bandwidth of the noise.
Figure 6B:
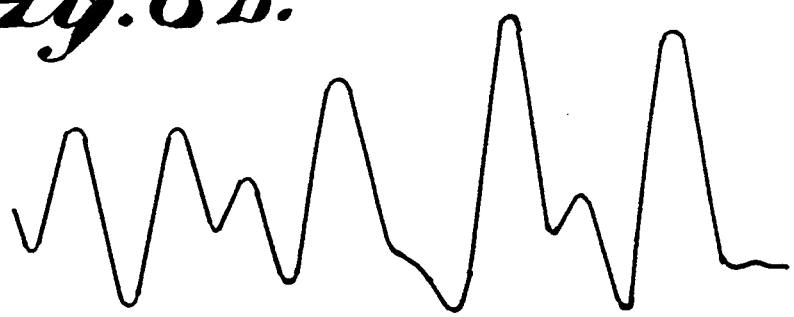
Figure 6C:
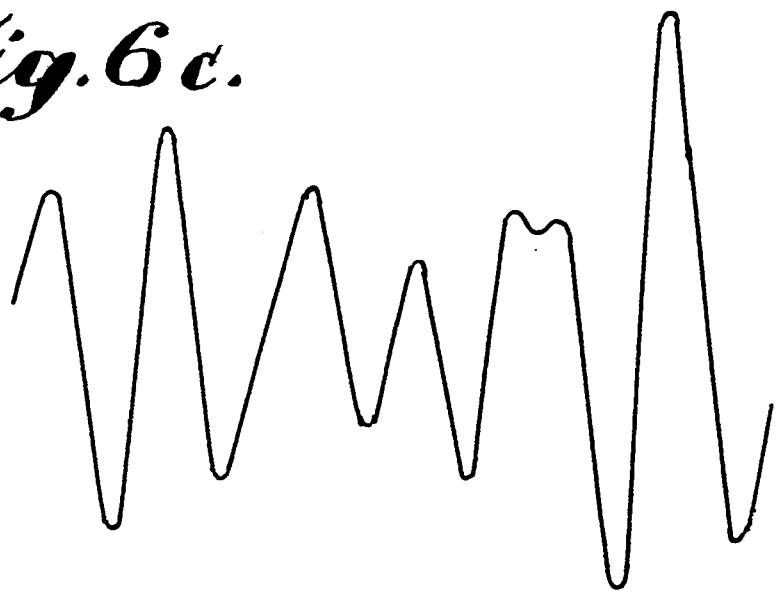

Referring to FIG. 6a, a sinusoidal signal is depicted. A superimposed bioprotection field source which has an field in the shape of random noise is depicted in FIG. 6b. FIG. 6c is the resulting bioprotected field surrounding the living system because of the combination of the sinusoidal signal of FIG. 6a and the bioprotecting field signal of FIG. 6b.

Figure 7A:
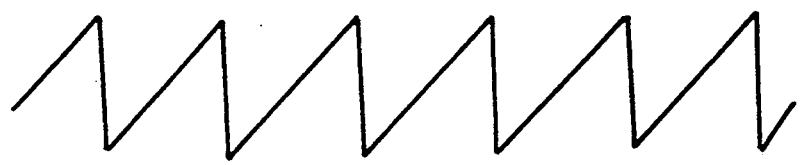
FIGS. 7a, 7b, and 7c provide a representation of the effect of superimposing a band limited noise signal over a sawtooth signal whose frequency is within the bandwidth of the noise.
Figure 7B:
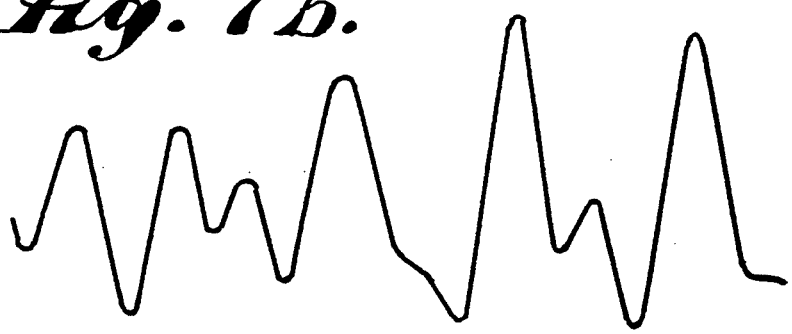
Figure 7C:

FIG. 7 shows the effect of the modulation of a sawtooth waveform by superposition of a band-limited random noise signal. Referring to FIG. 7a, a sawtooth signal is depicted. FIG. 7b depicts a superimposed bioprotection field source which has an field in the shape of random noise, and FIG. 7c is the resulting bioprotected field surrounding the living system because of the combination of the sinusoidal signal of FIG. 7a and the bioprotecting field signal of FIG. 7b.

There are essentially two types of embodiments of this invention: (1) direct modulation devices which are placed in the electrical circuit of the source of the detrimental field; and (2) superposition devices which are independent from the detrimental field source but create a confusion field which is intended to be combined with the detrimental field, creating a bioprotected field.

DIRECT MODULATION EMBODIMENTS

The direct modulation embodiments demonstrate the many possible methods of directly modulating a regularly oscillating current to minimize its bioeffecting properties. FIG. 8 is a block diagram which explains the general scheme of the direct modulation technique of this invention.

Figure 8A:
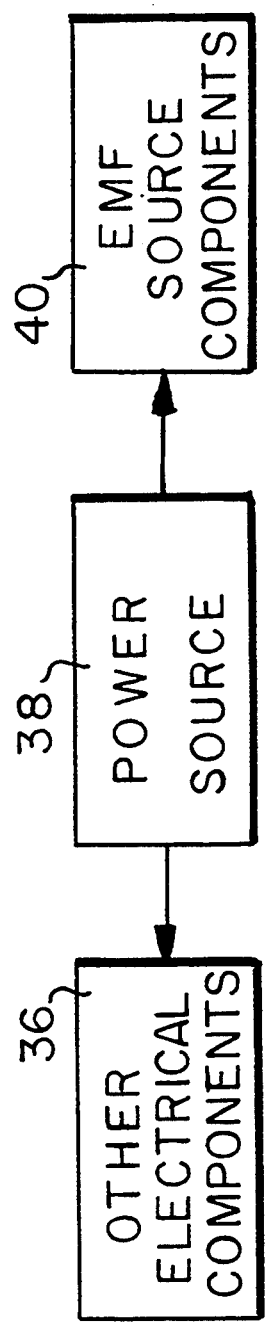
FIGS. 8a and 8b provide a block diagram representation of the direct modulation implementation of the bioprotection feature of the inventions.

Referring to FIG. 8a, a standard electrical device contains electrical components which produce field 40 and those electrical components which do not produce field 36. All electrical components require a power source 38 to operate. Therefore, as seen in FIG. 8b, one type of embodiment of the inventions places an in-circuit modulator 42 between the power source 38 and the detrimental field producing components 40.

Figure 8B:
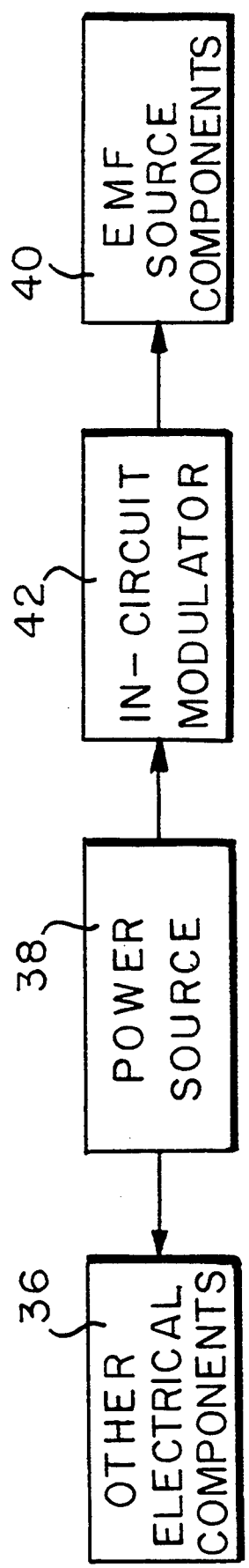
Figure 9:
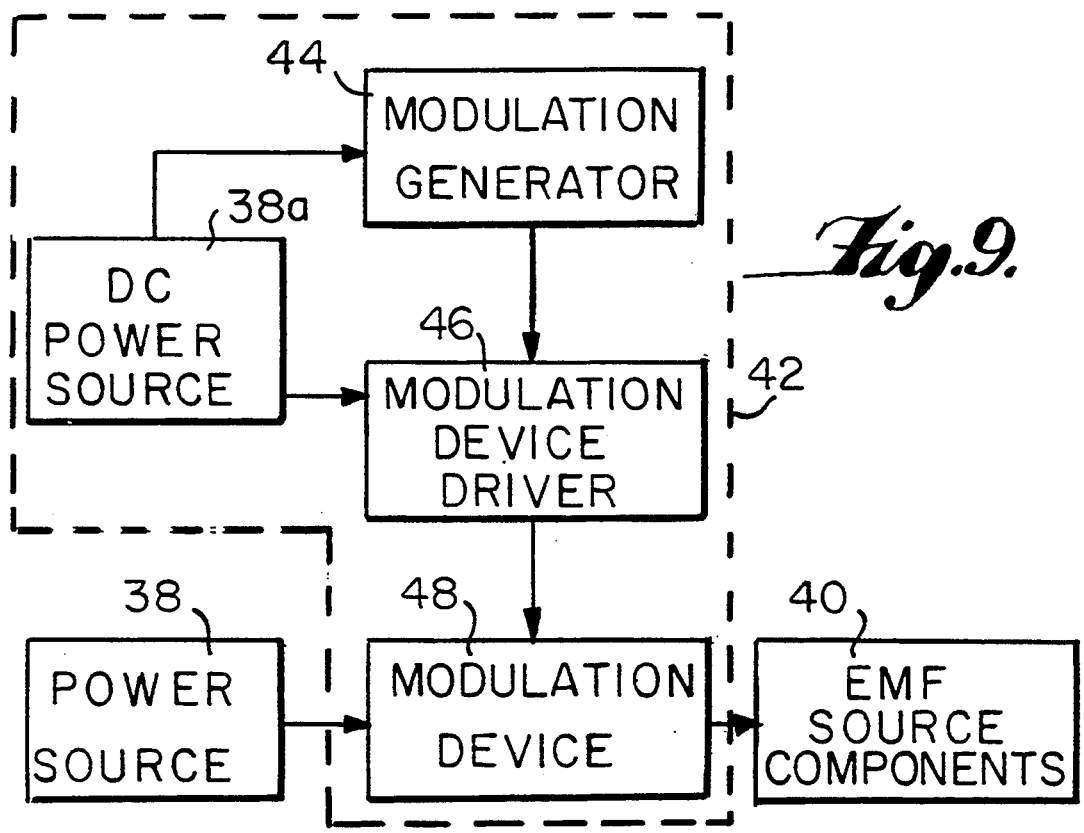
FIG. 9 is a block diagram representation of the in-circuit modulator of the direct modulation implementation of the bioprotection of the inventions.

FIG. 9 is a block diagram which explains further the in-circuit modulator 42 of FIG. 8b. The in-circuit modulator 42 directly modulates the power flowing into an electrical circuit so as to render its emanating field harmless (bioprotected field). A power source 38 supplies power to the field source components 40 and the circuitry of the in-circuit modulator 42. The in-circuit modulator comprises a modulation generator 44 which creates a modulating waveform in accordance with this invention. The Modulation device driver 46 powers the modulation device 48. The modulation device directly modulates a fundamental property of the power source 38, and then the resulting bioprotected power source powers the field source components 40. Because the power source has a fundamental property which is modulated according to this specification, the resulting field from the field source components, which would otherwise be detrimental, is then rendered bioprotected.

The DC power source 38a represents any DC source of electrical power, for example a battery, an AC line transformer, and an AC line capacitively coupled DC power supply. The transformer isolated supply can have large field's in the vicinity of the transformer. However, these fields are mostly localized. The AC line capacitor coupled DC power supplied can become rather inefficient if the power requirement is large. An AC line powered transformer isolated regulated DC power supply is easily constructed using a suitably rated transformer, a half wave or full wave rectifier, a charging capacitor, and a voltage regulator such as one of the LM78XX line manufactured by National Semiconductor. An AC line powered capacitor coupled regulated DC power supply is easily constructed using for example a MAX610 or MAX611 AC to DC converter IC from Maxim Electronics. One disadvantage of the capacitively coupled DC power supply is that it is not isolated from the AC line.

The modulation generator 44 may be implemented as a timing circuit. There are many possible implementations of a timing circuit. One alternative is to use a crystal oscillator to generate a base clock frequency. The period and duty cycle of the control signal may be set by using the appropriate frequency dividers and combinatorial logic. Another alternative is to use a monostable multivibrator circuit such as the one based on a 555 timer. An implementation of this circuit is given in data books published by National Semiconductor, and are well known in the art. The period and duty cycle are easily changed in this circuit in the range 50–100%. The complement of the output signal obtained by means of an inverter, such as the 7404, can be used for values outside this range.

The timing circuit may also be implemented using a microprocessor. Microprocessors and microcontrollers are digital devices which can perform a multitude of arithmetic and logic operations under software control. More complex timing schemes may be achieved using a microprocessor, for instance, the duty cycle of the square wave may be randomly varied, however, there is no inherent advantage in the use of these complex timing sequences as far as the effectiveness of the bioprotecting action is concerned.

The modulation device driver 46 constitutes the interface between the modulation generator 44 and the modulation device 48. This component should ideally provide line isolation to eliminate any possible feedback from the load current to the control logic. A possible implementation is an optoisolated triac/SCR driver such as the MOC3030 made by Motorola.

The modulation device 48 controls a fundamental property of the power source through the load. The modulation device 48 may be a switching device in the case of current modulation, but because of switch cycling and overall operating lifetime requirements, this component must typically have a life time of at least one billion switching cycles. Solid state switches implemented with triacs or SCR's are ideally suited for this application. An example of a suitable triac for 115 V operation is one of the MAC3030 series made by Motorola.

SUPERPOSITION MODULATION EMBODIMENTS

Figure 10:
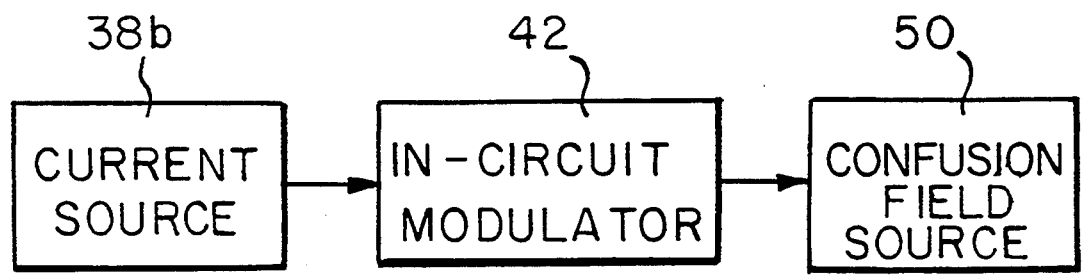
FIG. 10 is a block diagram representation of the superposition modulation implementation of the bioprotection feature of the inventions.

Another technique and device for implementation of the inventions is to superimpose a confusion field signal upon the detrimental field. The source of the confusion field can be a coil driven, for instance, by circuitry similar to that used for the direct modulation scheme. The confusion field created by the coil or otherwise field producing device, is used to superimpose an appropriate confusion field over the ambient detrimental field. The general scheme of this technique is depicted in FIG. 10. Referring to FIG. 10, a confusion field source 50, typically a coil structure, is placed in proximity to the detrimental field and the living system to be protected. The confusion field source 50 is then powered by a current source 38$b$, with the current from source 38$b$ modulated by at least one fundamental property through an in-circuit modulator 42 of the type described in this specification.

As previously noted, to be effective the amplitude of the bioprotection signal must be at least as large as that of the detrimental field. One approach to meet this requirement is to establish a signal level high enough to cover the normally expected magnetic field fluctuations. Alternatively, in cases where the ambient magnetic field is expected to vary, the bioprotection signal level could be adjusted in response to changes in the average magnetic field.

It has been experimentally shown that the bioprotection field need not be continuously present to be effective. For instance, a bioprotection periodic signal which is turned on and off in subsequent one second intervals is still effective. This property is useful in implementing a bioprotection scheme which is responsive to changes in the magnetic field environment. During the signal off time the bioprotection coil may be used to measure the prevailing magnetic field. A coil can accurately measure only magnetic fields which are uniform across the area circumscribed by the coil. If the bioprotection coil is large it would measure an average magnetic field, that is, the effects of localized fields would, in general, be averaged out. If the prevailing magnetic field environment is in large part due to a source producing a wide range magnetic field, such as a high tension power line, the coil measurement would be more indicative of the actual conditions.

One embodiment of the superposition modulation technique uses the embodiment of the direct modulation scheme, depicted in FIG. 10. In one case the fundamental property of the current from the current source chosen to be modulated would be amplitude, but it could be some other fundamental property such as frequency. But modulated coherent signals, other than line frequency signals, are more difficult to generate and therefore are not a convenient choice.

Figure 11:
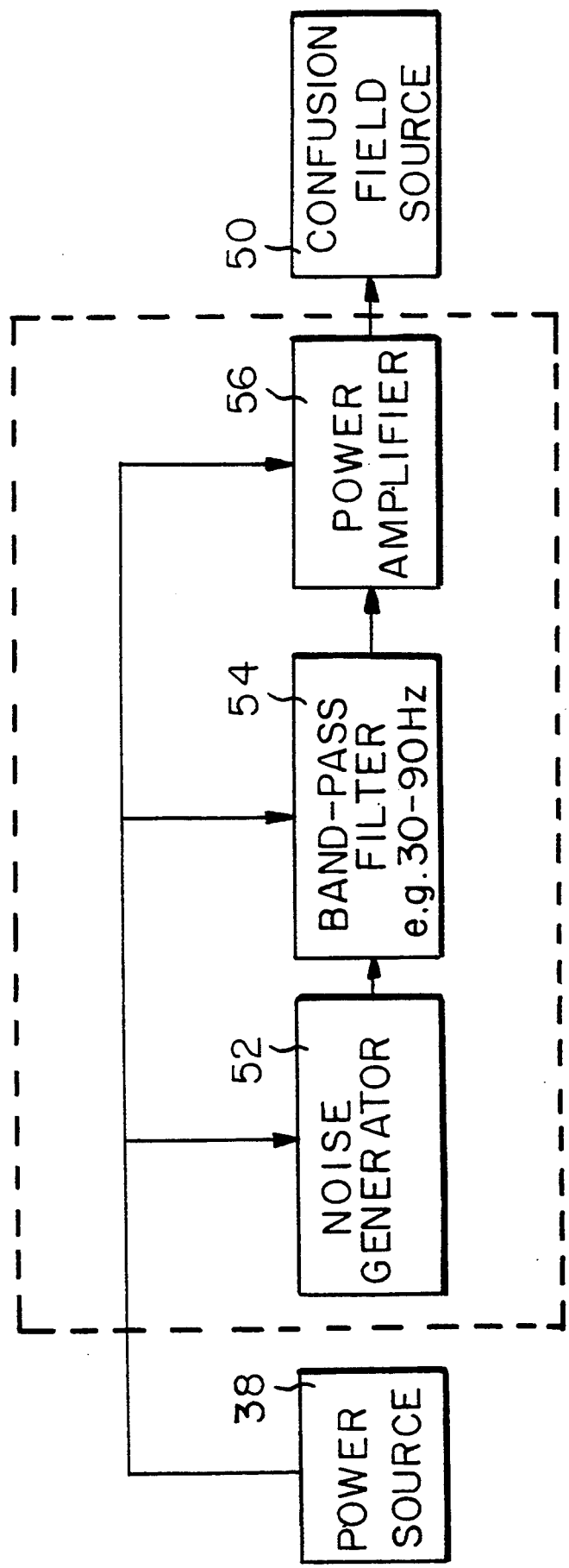
FIG. 11 is a block diagram representation of the in-circuit modulator of the superposition modulation implementation of the bioprotection feature of the inventions.

Another technique of superposition modulation is depicted in FIG. 11. This technique employs a noise generator 52 followed by a band pass filter 54 and power amplifier 56. These devices are powered by a power source 38, and drive a confusion field source 50, e.g. a coil or similar field radiating device. The components of this scheme are described in the following paragraphs.

If the power requirements are low, the power source 38 may be implemented using one of the methods described above. Standard methods described in the literature (e.g., National Semiconductor Linear Applications Handbook) may be used for applications with higher power requirements.

There are many techniques to generate noise signals for use as the Noise Generator 52. The following methods are suitable for situations in which the implementing circuit should not add significantly to the overall size of the application.

A noise signal may be generated by amplifying shot noise from a solid state device such as a zener diode. Electric current is defined as the flow of discrete electric charges. Shot noise results from statistic fluctuations of the current due to the finiteness of the charge quantum. The noise generated in this case is white Gaussian noise. An alternative means to produce noise is using digital techniques. A pseudo random digital sequence may be generated using a bank of n shift registers in which the output register is logically combined with one or more previous registers and feedback to the input register. Long sequences which are apparently random can be generated in this way. The sequence repeats itself after $2^n - 1$ shift cycles. It is easily seen that the shift register length can be made large enough to make an essentially random bit generator over the time of use of the sequencer. This circuit has been implemented in a special purpose IC, the MM5437 from National Semiconductor, which can be used as the noise generator for the application described herein.

The effectiveness of a confusion field is based on the premise that the biosystem senses the changing characteristics of the bioprotection signal and does not initiate a bioresponse. Based on experimental evidence, supported by the dielectric properties of biological cells, biosystems are more responsive to ELF fields. Therefore the bioprotection signal is expected to be sensed more effectively when operating in the ELF frequency range. Noise generation as described in the previous paragraph results in a wide band signal which must be filtered to produce a signal in the ELF range. Experimental evidence indicates that a noise signal with bandwidth between 30 and 100 Hz can be effective in inhibiting the bio-response when the rms amplitude of the noise is equal to or larger than the rms amplitude of the coherent signal. A bandpass filter 54 may be implemented either with a passive element network or with op-amp based circuits. The op-amp implementation is simpler having less components for an equivalent filter. There are various types of band-pass filter 54 implementations using op-amps: amongst them Butterworth, Chebyshev and Bessel filters. The sharpness of the response may be increased by increasing the number of poles of the transfer function of the filter. A 2-pole low pass Chebyshev filter designed to have a 0.5 Db ripple on the pass band was found to be one possible adequate implementation for this application. In this implementation the low frequency cut-off for the bandpass filter 54 at the specified frequency of 30 Hz is set up by the natural response of the circuit components.

Because of the ability to perform mathematical operations, a microcontroller may be used as the modulation generator 44. Confusion field signals designed to have amplitude or frequency changes or both over specific ranges of each period may be easily generated under software control. Likewise, a noise signal may be digitally generated with an algorithm which mimics the shift register noise generating implementation described earlier, or using other standard techniques. The bandpass filter 54 may also be performed digitally to reproduce the Chebyshev filter hardware implementation previously described or any other suitable filter implementation. In all these cases the output of the microprocessor controlled modulation generator signal dictates the current signal which is passed from the current source 38b to the confusion field source 50.

Amplification of the modulated signal may be achieved using an amplifier module of the same type already described. A power amplifier 56 may be necessary to power the confusion field source (i.e. a multiple turn wire loop or coil). The output of the bandpass filter 54 is typically not suited to drive a low impedance complex load such as a coil. A power amplifier 56 is needed to allow adequate current flow through this load. The power amplifier 56 design depends on the current requirements. Two power amplifier IC's covering a wide power range are the 7 Watt LM383 and the 140 Watt LM12, both made by National Semiconductor. Other standard op-amp based amplifier circuits are available in the general literature.

The confusion field source 50 must be designed to induce the desired confusion field within the region where the detrimental field is to be bioprotected. It should be noted that experimental evidence shows that the direction of the bioprotecting magnetic field is not important relative to the bioeffecting field. This allows some freedom in the design of the confusion field source 50. The selected configuration for a particular application also depends on space constraints, for instance if the confusion field source is to be incorporated as part of an existing electrical device without changing its general external configuration. In cases where bioprotection from a localized field arising from a small electrical device is sought, the confusion field source 50 would, for instance, be designed to surround the detrimental field source, or be strategically located in the proximity of the detrimental field source. Situations in which the range of the detrimental field is large, for instance with the large heating coils in electrically heated homes, or within power line fields, may require a much larger range of protection. Large coils circumscribing the area to be protected would be adequate in this case. Multiple coils would be necessary when the required range of protection is large in all dimensions as would be the case in a multi-story building.

Figure 12:
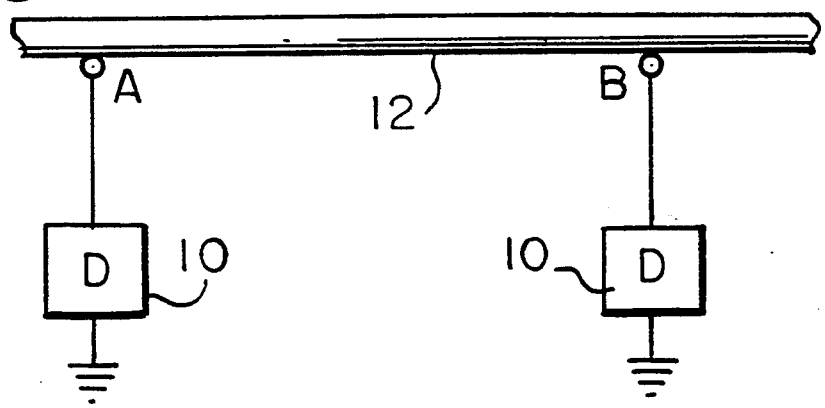
FIG. 12 is a diagram of a circuit for modulating electric current through a plumbing pipe.

Protection from leakage currents running through copper plumbing may readily be achieved, as shown in FIG. 12. With reference to FIG. 12, devices 10 are switches either electronically or mechanically controlled which switch on and off at intervals of one second (e.g. one second on and one second off). During the "on" intervals this will cause some of the current flowing past point A and B in the copper pipe 12 to alternately flow through ground rather than entirely through the pipe. Thus, the current flow from A to B (which creates an electromagnetic field in the working and living spaces of the structure) will be modulated (by reduction in current) at intervals of no greater than one second. The number of devices needed will depend on the complexity of the piping.

Figure 13:
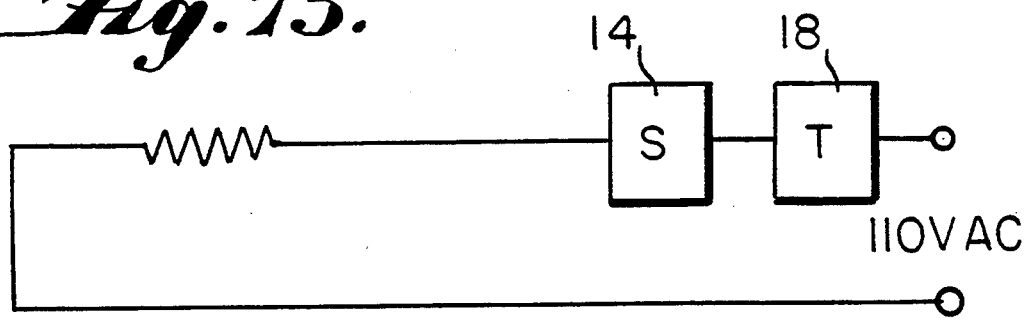
FIG. 13 is a diagram of a protective circuit for an electric blanket.

Protection from electric blankets is readily achieved. FIG. 13 shows the heating circuit of the electric blanket. Device 14 (the protective circuit) is a switch which turns the electric current through the blanket 16 on and off at intervals of one second. The device 14 need not switch the current completely off. It could, for example, reduce the current by 50 percent, and then within one second return the current to its full value. The device 18 is the usual thermostat supplied with electric blankets. Neither the "on" nor the "off" interval should be greater than 5 seconds, and should be preferably one second.

Figure 14:
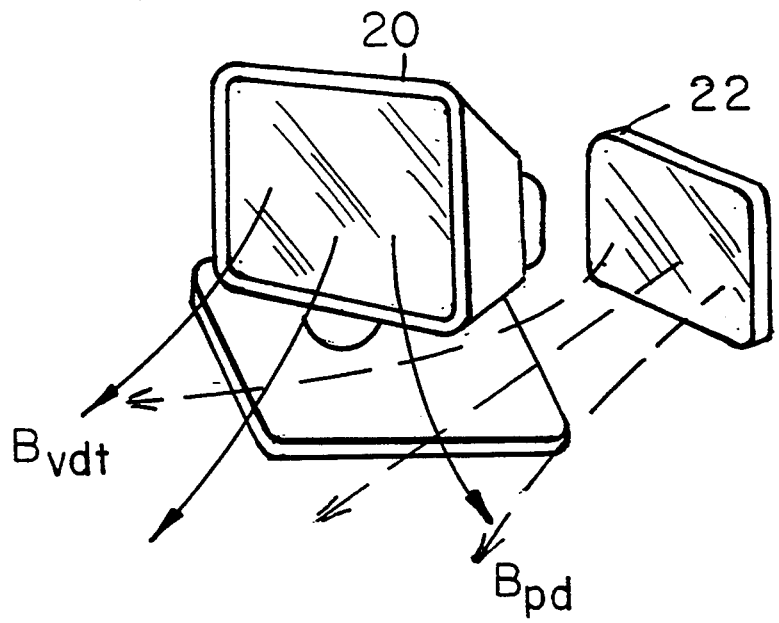
FIG. 14 is a diagram of a protective apparatus for use with a video display terminal.

Harmful effects of video display terminals may be avoided, as shown in FIG. 14. Referring to FIG. 14, the video display terminal 20 is protected by a source 22 of electromagnetic field. $B_{VDT}$ and $B_{PD}$ are, respectively, the magnetic fields of the video display terminal (VDT) and the protective device (PD). The average amplitude of $B_{PD}$ at any point in the region to be protected should be greater than 50 percent of the amplitude of the field due to the VDT. Preferably, the average amplitude $B_{PD}$ should be at least twice the amplitude of $B_{VDT}$. If the protective field of PD is in the same direction as the VDT field it will be most effective. If the PD field is perpendicular to the VDT field, it must be five times larger than the VDT field.

Figure 15:
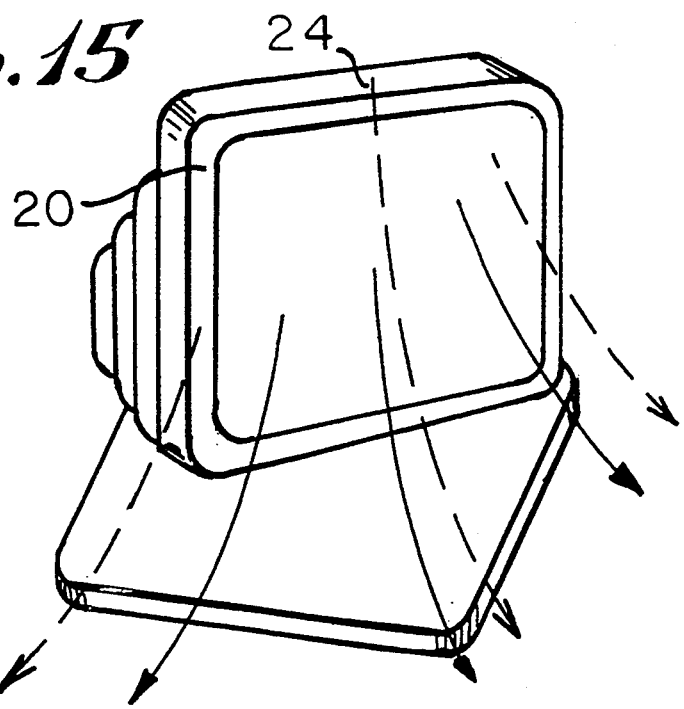
FIG. 15 is a diagram of another form of protective circuit for use with a video display terminal.

FIG. 15 shows a system similar to that shown in FIG. 14, however FIG. 15 shows the PD 24 as a coil mounted around the VTD 20.

The protective device can be any device which generates a time varying modulated electromagnetic field. For example, if a coil with ten turns of wire is to be used, it can be mounted either as in FIG. 14, or in FIG. 15. In FIG. 14 the coil is placed on a surface near the VDT and oriented so that its field intersects the field of the VDT. In FIG. 15 the coil is placed around the outer edge of the front of the VDT. In a typical VDT the coil could be a square about 40 cm on each side. The average current in the coil should be adjusted so that the average field at the front and center of the monitor due to the coil is preferably about equal to that field at the same point due to the VDT. For example, if the average field at the very front of the monitor is 10 $\mu$T a 10 turn coil of wire 40 cm on edge could have a 60 Hz cw current of approximately 0.35 amps flowing through it. The current could be alternatively 0.5 amps for 1 second and then 0.2 amps for 1 second.

It will be understood that a standard TV set (one case of VDT) can be protected in the same manner as VDTs or "computers". Oscilloscopes may similarly be protected.

Figure 16:
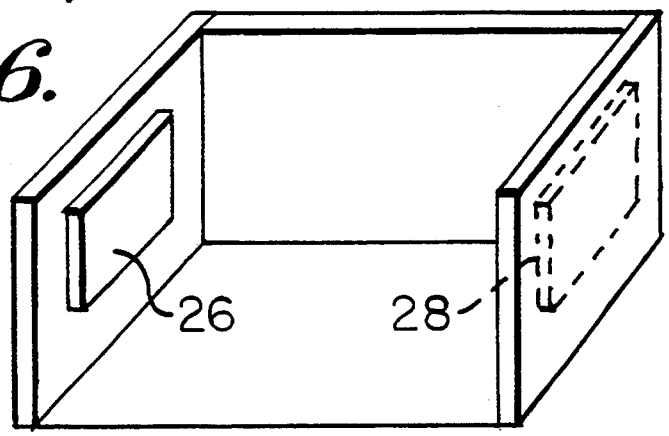
FIG. 16 is a diagram of a protective system for use in a space occupied by humans and/or animals.

Large areas may also be protected, as shown in FIG. 16. Referring to FIG. 16, large coils of wire 26, 28 (e.g. 7 ft high by 7 ft wide) are mounted on or near opposite walls of a room, or on the floor and ceiling. The latter configuration is more effective than the former when the ambient fields are in a vertical direction. It is assumed that the room is exposed to a cw electromagnetic field that is dangerous to living systems. Modulated current (e.g., "on" and "off" at one second intervals) flows through the coils. The current and the modulation in coil 26 is kept in phase with the current and modulation in coil 28. The pair of coils act as Helmholtz coils and tend to keep the field in the protected region more uniform than if a single coil were used. The average amplitude of the current in the coils should be such that the electromagnetic field produced by the coils at every point in the region to be protected is at least 50 percent of the ambient field and preferably 5 to 10 times the ambient value.

A single coil can be used instead of the a pair of coils. The larger the coil the better; a larger coil will provide a more uniform protected region than a small one.

Figure 17:
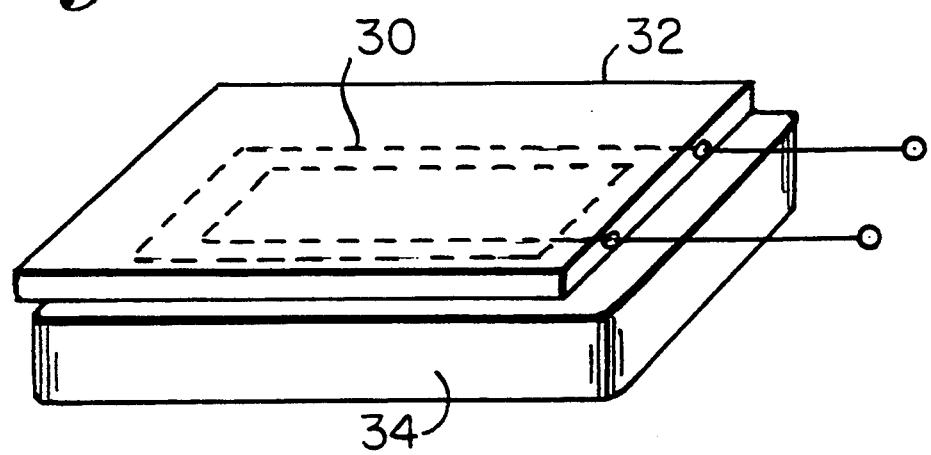
FIG. 17 is a diagram of a mat for placement on or under a mattress used for sleeping purposes.

Special mats containing coils can be used in the home, laboratory, or other living system inhabited place to provide general protection. For example, a large percentage of the time spent at home is by a human sleeping on a bed. Thus, it would be useful for those who live near power distribution lines to use a device which puts the human in a protective "confusion" field during the time during which he is lying on the bed. FIG. 17 shows the use of a coil structure to produce a confusion field in a mattress.

As shown in FIG. 17, this can be done by embedding a many turn coil of wire 30 in a mat 32 and placing this mat either on or under the mattress 34, but near the head of the bed for maximum protection of the vital organs. The wire should be of low resistance, since it would be used year round and should not have significant heating of the bed or its occupants. This coil of wire would have the modulated current flowing through it during all seasons. The modulated electromagnetic field would protect the occupants of the bed from the ambient electromagnetic fields in the room. For example for a queen size bed a square coil of wire with 10 turns approximately 60 inches by 60 inches square and with 0.14 amperes of current flowing will yield at the center of the coil a magnetic field in the vertical direction of about 1 micro Tesla. If the bed is over 100 feet away from a power line 20 feet in the air, the ambient magnetic field due to the power line is also in the vertical direction. Thus, we have an optimum alignment of the field of the coil and that of the power line. To create a confusion field the current in the coil should vary from about 0.03 amperes to 0.07 amperes and back at least once every second yielding a coil field at the center which fluctuates between 0.5 and 0.2 $\mu$T. Assuming that the power line is 1 $\mu$T, the total field near the center will (if the coil field is in phase with the power line field) change from 1.2 $\mu$T to 1.5 $\mu$T and back every second. If the fields are out of phase the net field will vary from 0.5 to 0.75 $\mu$T every second. Either of these conditions would protect the occupants from exposure to the power line field. The above coil could be combined within an electric blanket so that the blanket would serve a dual purpose of heating and protecting.

Such mats also may be adapted for use with chairs, or placed on tables or kitchen counters, or wherever humans or animals spend considerable time.

CONVERTER BOX EMBODIMENT

The converter box is an embodiment which employs the direct modulation technique of this invention. Electrically powered devices operating at power line frequencies and using resistive type elements to generate heat are always surrounded by a magnetic field induced by the flow of electric current through the heating element(s). The magnitude and range of the magnetic field emissions are a function of the geometry of the heating element(s) and the amplitude of the current passing through it. The present embodiment makes use of the direct modulation technique in a general purpose device which converts line power into a minimally bioeffecting format. Because of its function the device is herein after called the 'converter box'. Its use is as an add-on bioprotection module for standard resistive type heating devices.

Figure 18:
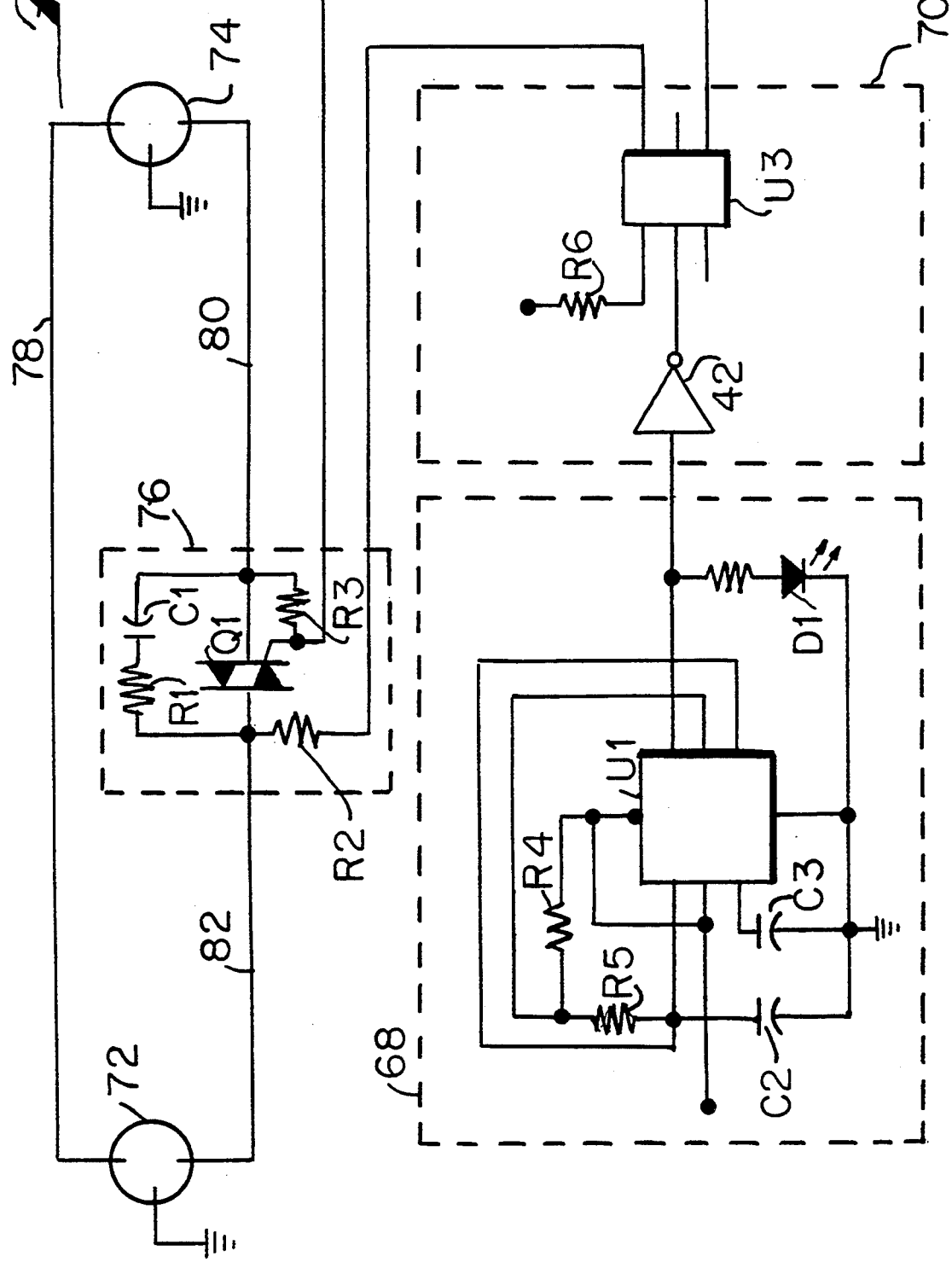
FIG. 18 is a circuit diagram of a direct modulation bioprotective converter box.

FIG. 18 shows the circuit diagram for a converter unit which modulates the fundamental property of amplitude of standard household electrical current, for use by an external appliance. Referring to FIG. 18, the converter box is designed for connection to a standard household power line outlet, for instance a 120 V, 60 Hz outlet, either directly through an integral plug or via a power cord 74. The line power is then modulated within the converter box using one of the methods for direct modulation previously described and made available in its modulated form through a power outlet on the converter box. The electric and magnetic field emissions from a resistive type heating device operating from the modulated outlet of the converter box are similarly modulated and therefore become negligible bioeffectors.

The converter box may be used, for example, with electric blankets, electric heating pads, curling irons, and other low power resistive heat devices. Use with devices incorporating fan motors or other inductive loads is not recommended, because line power modulation may cause improper operation of an inductive load. One possible circuit implementation of the converter box is shown in FIG. 18. This implementation uses a 1 second period and a 90% duty cycle. If no power loss is desired from the bioprotection modulation the switching device may be implemented as a DPDT switch connecting either to the line frequency or to a full wave rectified line frequency signal.

The converter box is plugged into a power source 74, e.g. a household circuit. The switching device 76 intercepts the hot line 80 of the power source 74, while the neutral line 78 is jumpered directly between the power source 74 and the bioprotected outlet 72. The switching device 76 resides between the hot line 80 of the power source 74 and the hot line 82 of the bioprotected outlet 72. The converter box implements a control signal generator 68 and a switching device driver 70 in conformance with the disclosure of direct modulation methods described herein.

BIOPROTECTED THERMOSTAT EMBODIMENT

Figure 19:
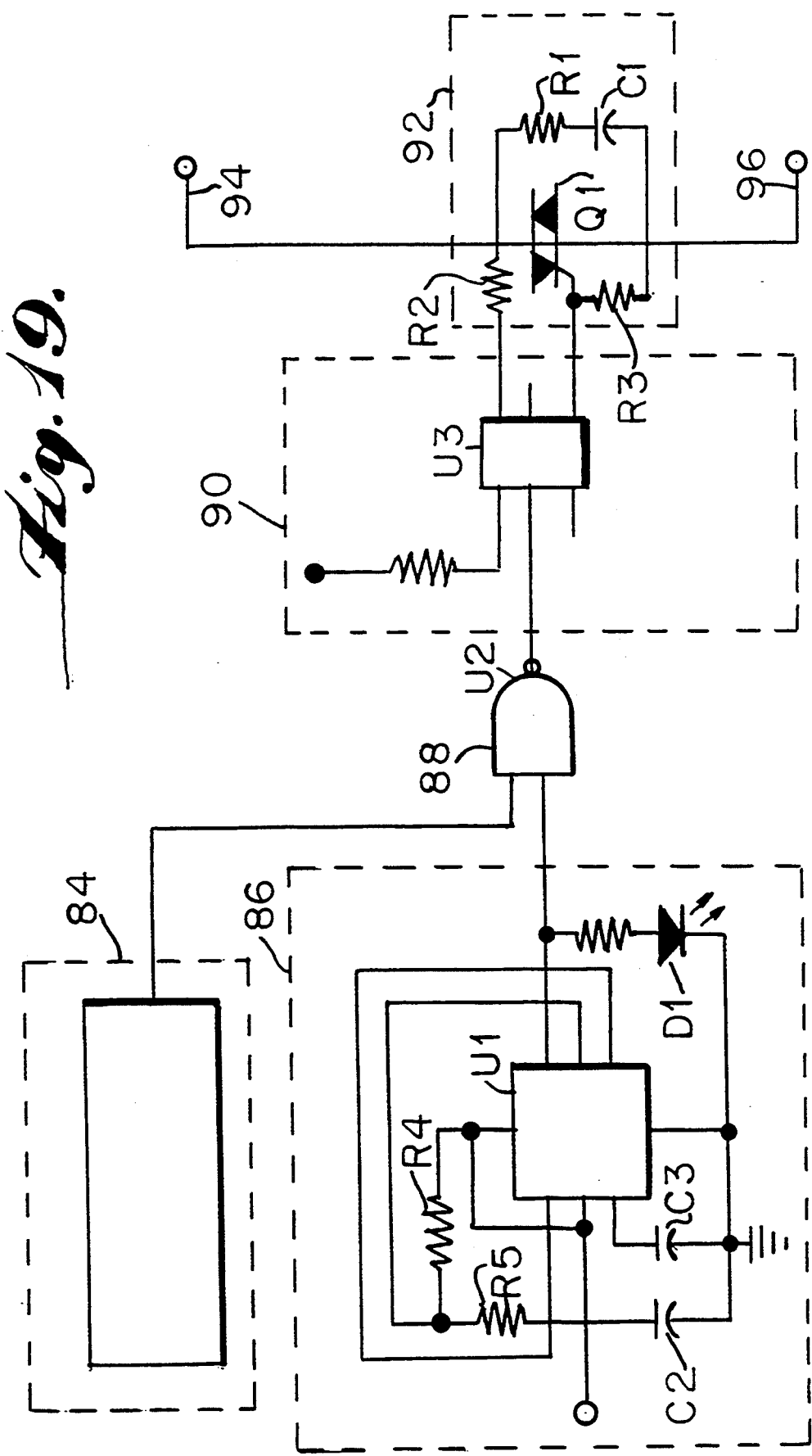
FIG. 19 is a circuit diagram of a direct modulation bioprotective thermostat.

In-line thermostats are devices used to control current flow in response to changes in temperature relative to a set level. Although many circuit designs are possible to implement the inventions described herein, one will be described. The circuit for an embodiment of a thermostat is depicted in FIG. 19. In this embodiment, current control is achieved by means of a modulation device 92. Control of the modulation device 92 is achieved through the use of a modulation device driver 90, along with a temperature control circuit 84, and modulation generator 86. The temperature control circuit 84 and the modulation generator 86 are NANDed together and input to the modulation device driver 90. One possible implementation of the modulation device driver 90 uses a triac, such as the MAC3030 or MAC3031 made by Motorola or another suitably rated unit, for the switching device. The modulation device driver 90 would be controlled by logically NANDing a signal from a temperature control circuit 84, (e.g. a circuit using an LM3911 temperature controller made by National Semiconductor), and a signal from a modulation generator 86. The modulation generator 86 may be implemented using a 555 timer connected as a monostable multivibrator. The simplest method to implement the bioprotection feature is by periodically switching off the field. A duty cycle of 90% with a period of 1 second could be used to minimize the effect of the modulation on the heating efficiency. If no heating loss is desired from the modulation, the latter may be implemented by switching between no rectification and full wave rectification. However, in this case the modulation device 92 controlled by the temperature control circuit 84 would be connected in series with the modulation device driver 90 and would operate independently from the latter. The lines 94 and 96 into the modulation device 92 complete the circuit to the load for which thermostatic control is desired.

BIOPROTECTED HAIR DRYER (Superposition Modulation Technique) Embodiments

Hair dryers, like other electrically powered devices operating at power line frequencies and using resistive type elements to generate heat, cause magnetic fields induced by the flow of electric current through the heating element(s). Most hair dryers operate by blowing heated air through a large nozzle. The air is heated as it passes through a set of heating coils mounted within the nozzle. The primary sources of magnetic field emissions are the heating coils, and the fan blower motor. In normal operation the nozzle of the hair dryer is pointed towards the head. Therefore, the magnetic field emissions from the heating coil at the head of the user, are often larger in magnitude than those from the fan motor. The magnetic field emissions from most standard hair dryers are of relatively high amplitude and are therefore bioeffecting fields. The embodiment described in this section incorporates the bioprotection features of the inventions into a standard hair dryer. In addition, a heating coil arrangement designed to have low magnetic field emissions is described.

In the present application the bioprotected feature may be incorporated either by direct modulation of the current that passes through the heating coils or by superposition modulation. In the case of direct modulation, the current passing through the heating coils can be modulated using one of the methods described in the direct modulation section, or the method described in the thermostat example above. In standard hair dryers, it is common to use a low voltage DC motor to drive the fan. The current through the motor is limited by a heating coil connected in series with it. When direct modulation is employed, as prescribed in this invention, the design of the hair dryer may require that the modulation be imposed in such a way that it affects only the current passing through the heating coils which are not connected in series with the motor.

A circuit similar to that of FIG. 19 would be appropriate, with a modulation device driver 90 selected to handle the power requirements of the hair dryer, e.g. incorporating the MAC3030-15 triac, manufactured by Motorola.

When the superposition method is used, the confusion field may be imposed using a confusion field source, in this case a coil structure, slipped over the heating coil(s) located within the nozzle of the hair dryer. The modulation device which drives the external coil may be modulated using any of the methods described herein for superposition modulation. One possible circuit implementation of the bioprotected hair dryer with superposition modulation is shown in FIG. 20.

FIG. 20 depicts a noise generator 98, with its resulting signal fed through a low pass filter 100, and then amplified enough by a power amplifier 102 to power the confusion field source 106 (in this case a coil structure).

A sensing circuit which detects, for indication to the user, that a confusion field is present can be implemented in any of the embodiments described herein. One possible circuit diagram for such a sensing circuit is shown in FIG. 21.

Referring to FIG. 21, the sense input 108 is a signal received from the confusion field source 50, such as the coil 106 in FIG. 20. In this embodiment, the existence of the confusion field is indicated by an LED 112.

Figure 22:
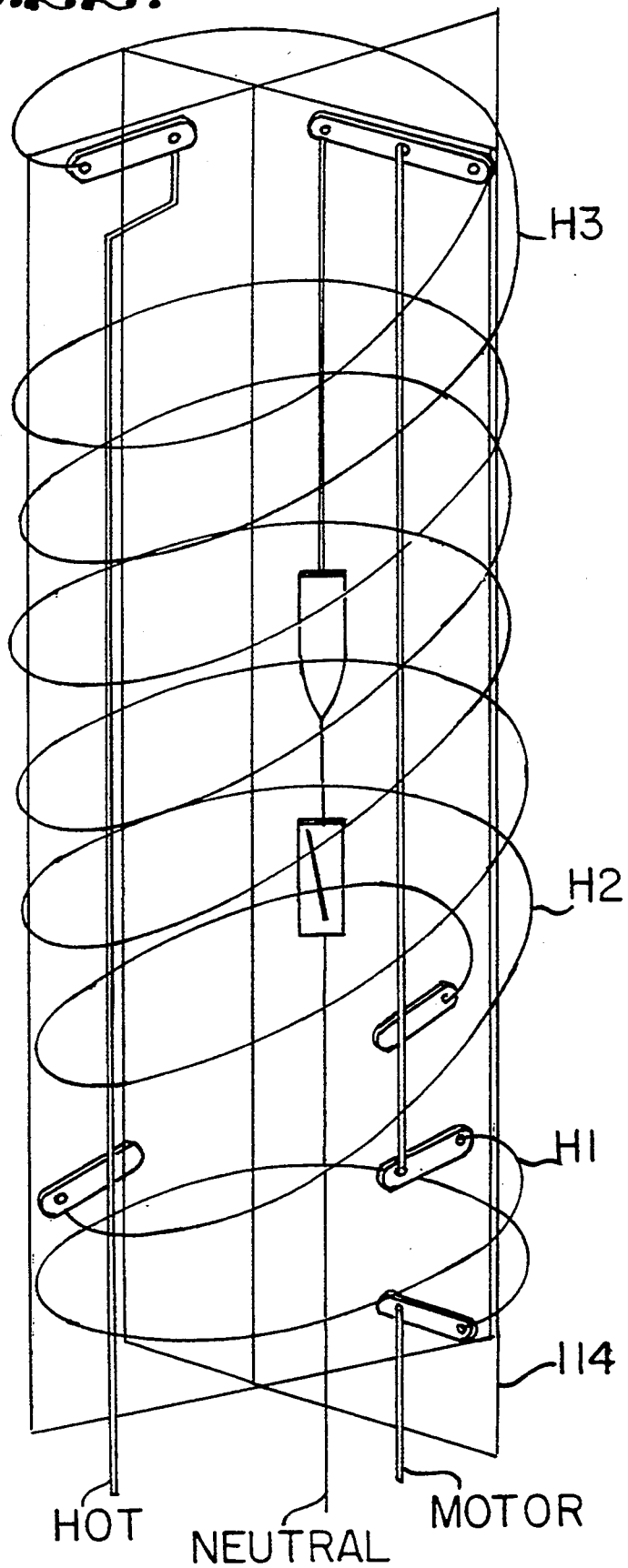
FIG. 22 is a heating coil configuration with low magnetic field emissions for a bioprotected hair dryer.

To reduce the power requirement to the confusion field source coil 106, it is preferable to design the heating coils for low magnetic field emissions. One possible configuration which achieves this goal is shown in FIG. 22. FIG. 22 shows the coil structure formed around a structure 114 made of mica. The coil H3 runs anti-parallel to coil H2.

Figure 23:
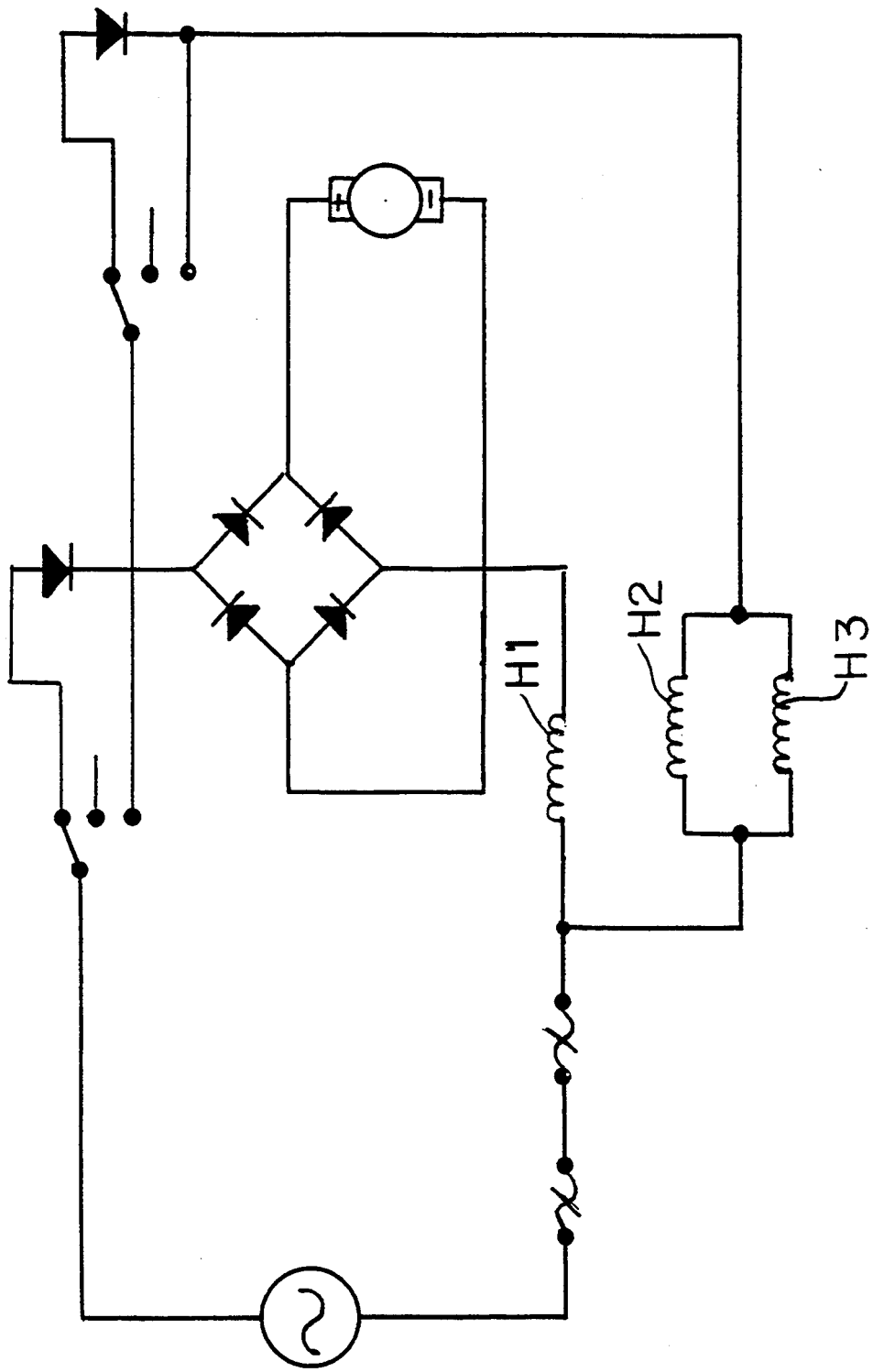
FIG. 23 is a circuit diagram for control of the heating coil configuration of FIG. 22.

FIG. 23 shows a circuit for controlling the heating coils of FIG. 22. In this configuration two heating coils, H2 and H3, are connected in parallel in such a way that equal currents run in opposite directions in each coil. This arrangement reduces the magnetic field emissions since magnetic fields are induced in opposite directions thus partially canceling each other. Coil H1 allows the use of a low voltage motor for the fan.

To most effectively inhibit the bioeffecting potential of the magnetic field from the heating coil, the external coil should produce a magnetic field oriented along the same direction as the heating coil field. This may be accomplished by winding a solenoidal type coil over the reflector shield which provides a thermal barrier between the heating coil and the nozzle plastic body. For a fixed number of turns, the external coil resistance may be adjusted by the choice of wire gauge. For instance, the driving circuit of FIG. 20 can produce a suitable bioprotection field when driving a 280 turn, 2 inch diameter, 14.5 $\Omega$ solenoidal coil made with 28 gauge wire.

BIOPROTECTED KEYBOARD EMBODIMENT

Video display terminals use magnetic deflection coils to control the vertical and horizontal scans. The magnetic field from the deflection coils are typically sawtooth waves oscillating in the neighborhood of 60 Hz and 20 KHz. The lower frequency emissions produce magnetic fields of the order of 10 $\mu$T at the center of the display screen. These fields are quickly attenuated with distance away from the screen. However, users often sit within a foot or so of the face of the monitor where the magnetic field can be in the range 0.4–2.4 $\mu$T (Hietanen, M and Jokela, K., "Measurements of ELF and RF Electromagnetic Emissions from Video Display Units", Work with Display Units 89, Ed. Berlinguet L. and Berthelette D., Elsevier Science Publishers, 1990). The higher frequency emissions, which fall within the RF range, produce magnetic fields which can be as large as 0.7 T at the center of the display screen. These fields decay to around 10–1010 nT at 12 inches from the face of the monitor (Hietanen '90). As previously noted, experimental evidence indicates that the bio-effecting potential of electromagnetic fields is more significant at lower frequencies. It has been shown that magnetic fields of the type used for the vertical scan control in video display terminals can produce biological effects even with levels as low as 0.5 $\mu$T.

The embodiment described in this section makes use of the superimposition principle delineated in the superposition modulation section to create a device which provides the bioprotecting effect of a confusion field in the region where a user would ordinarily be exposed to the magnetic field emissions from a video display terminal or other sources in the vicinity of the terminal. The device forms an integral part of a computer keyboard and is consequently referred to as a bioprotected keyboard. The coil structure for a keyboard of this embodiment is shown in FIG. 24.

Figure 24:
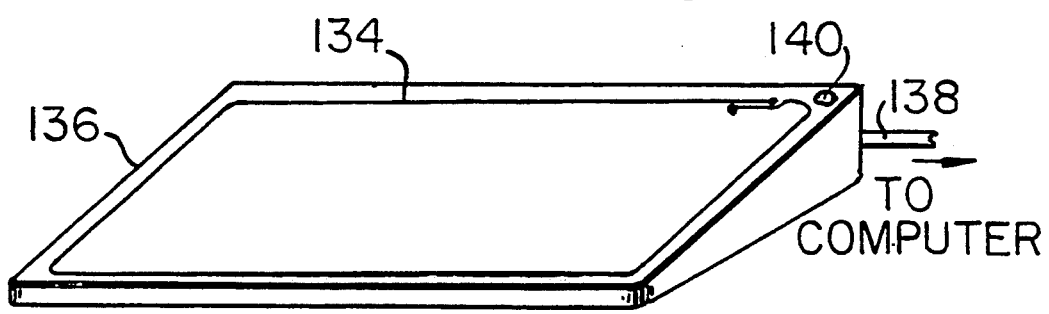
FIG. 24 is bioprotection coil for a computer keyboard.

Referring to FIG. 24, this device uses a coil 134 as its confusion field source 50, installed within a computer keyboard 136 and operated by circuitry integral to the circuitry of the keyboard. Power to operate the coil is derived from the host computer via the standard keyboard interface connection 138. The presence of the coil 134 does not interfere with any of the operations of the keyboard 136 and is transparent to the user except for an indicator LED 140 which advises the user of the proper operation of the bioprotection feature. Electric current, modulated as per the methods described herein, is passed through the coil 134 to induce a confusion field designed to bioprotect the field emissions from the monitor at the user location without interfering with the proper operation of the monitor. The coil 134 is driven by a in-circuit modulator 42 designed to inject suitable power into the coil 134 using one of various possible methods.

The range of protection of this device is ideally within approximately a foot or so from the keyboard, therefore it is most effective when the keyboard is held closest to the user. In some cases the detrimental field emissions from the monitor may be too high to be adequately bioprotected by a coil 134 powered from the standard keyboard power supply. In these situations it may be advantageous to drive the coil with an external power source. In the latter case the power driven through the coil can be made as high as necessary to produce the required confusion field according to this invention. A possible limitation to the power applied to the coil 134 is the possibility of jitter created on the screen display by the proximity of the coil 134.

The confusion field source may be implemented as a coil 134 concealed within the keyboard 136 as in FIG. 24, or it may be placed on top or near an existing keyboard. In general it would be advantageous to make the coil 134 as large as possible as this would increase the range of the magnetic field and decrease the power requirements. One possible means to increase the size of the coil 134 is by fitting the keyboard 136 with a large base to house the coil. In addition the coil resistance should be small enough to allow sufficient current flow from the available power source. As an example, a 6.5 inch by 17.25 inch 50 turn rectangular coil made with 28 gauge wire has a resistance of about 13$\Omega$. This coil can be satisfactorily driven with the circuit of FIG. 20.

HOME BIOPROTECTION SYSTEM EMBODIMENT

Another embodiment of the superposition modulation technique is the home bioprotection system.

Most homes have numerous sources of field, including all electrically operated devices. In addition, residences located in the proximity of high voltage tension lines are also subjected to the field emissions from those lines. These emissions can be significant in the vicinity of power lines of high current carrying capacity. Another source of field results from the flow of leakage current through ground paths. These leakage currents can in some cases be relatively large when they are caused by current imbalances created by unequal current usage between two phases of a circuit. In general, the high and low leads of a circuit run parallel and in close proximity to one another. This type of electric cable, e.g. Romex cable, is most often used in residential installations. Current flow through this type of cable induces magnetic fields of relatively short range. The magnetic fields decrease with distance away from the conductors as the inverse of the cube of half the distance between the leads. If the hot and neutral leads of a circuit run separated from one another, the flow of current through such a circuit can generate field which cover a wider range. These field emissions are relatively uniform within the area circumscribed by the wires and extend relatively unattenuated within a distance equal to one third the loop radius above and below the plane of the loop. The present embodiment describes a technique to negate the detrimental nature of these field fields by providing a blanket type protection covering the entire living area of a home.

Figure 25A:
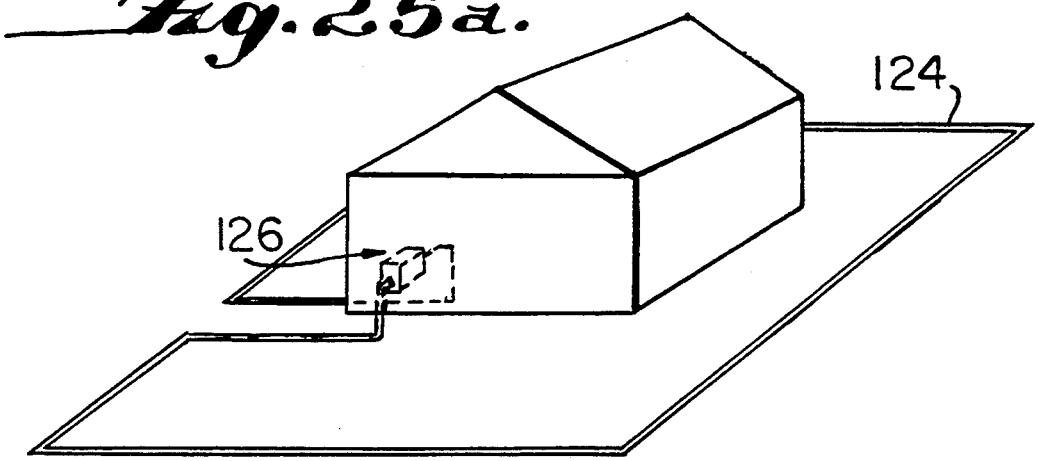
FIG. 25a is coil arrangement for a bioprotection system for a residence or other building.
Figure 25B:
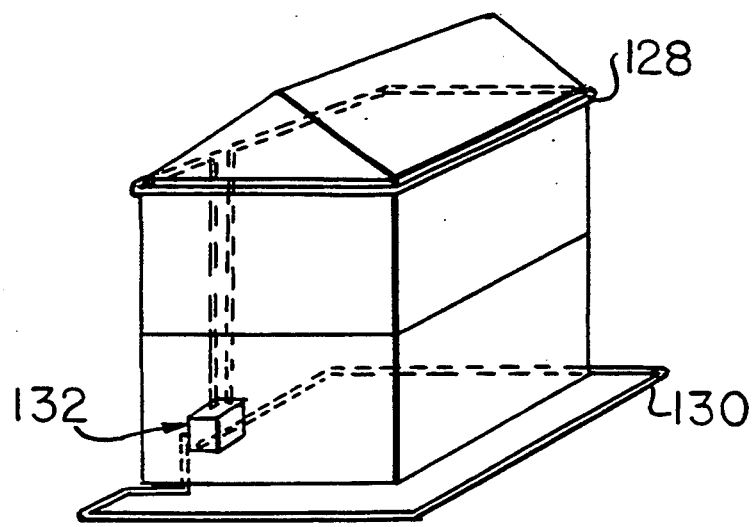
FIG. 25b is a circuit diagram of another possible implementation of a bioprotection system for a residence or other building.

The home/area bioprotection device consists of a large multiturn coil positioned in the perimeter of a residence, playground or other area to be protected. Two possible coil configurations for use in the protection of a home or large area are shown in FIGS. 25a and 25b. FIG. 25a depicts an underground coil structure 124 which surrounds the area desired to be protected. The control unit 126 is typically placed inside the house, or outside in a weatherproof container. The home bioprotection system coils 128 and 130 of FIG. 25b are of a helmholtz configuration, as described earlier. One coil 128 is placed above the living area, while the other 130 is placed below it. The control unit 132 is similar to the control unit 126 of FIG. 25a, however it typically drives two coils instead of just one.

Electric current, modulated as prescribed in this invention, is passed through the coils 124, 128 and 130 to induce a bioprotection magnetic field. The coils are driven by an in-circuit modulator 50 designed to inject a suitable current into the confusion field source (in this case a coil structure). The coil 124, 128 and 130 current may be generated using any one of the methods described above. One possible circuit implementation is shown in FIG. 26.

Figure 26:
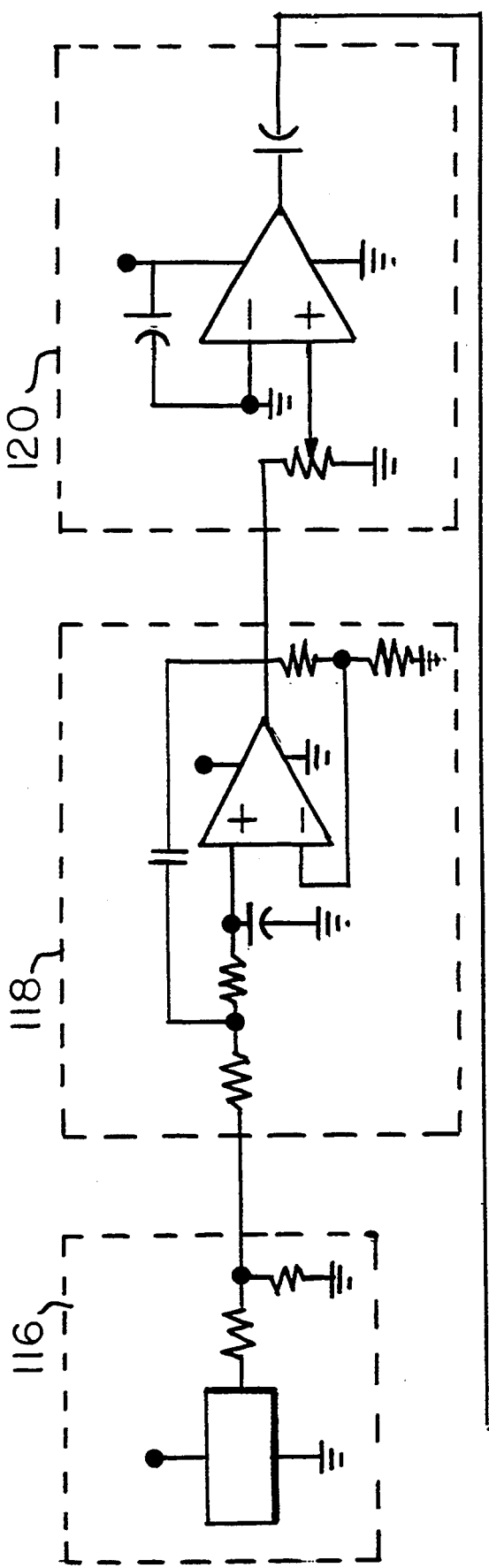
FIG. 26 is a circuit diagram for a bioprotection system for a residence or other building.
Figure 26:
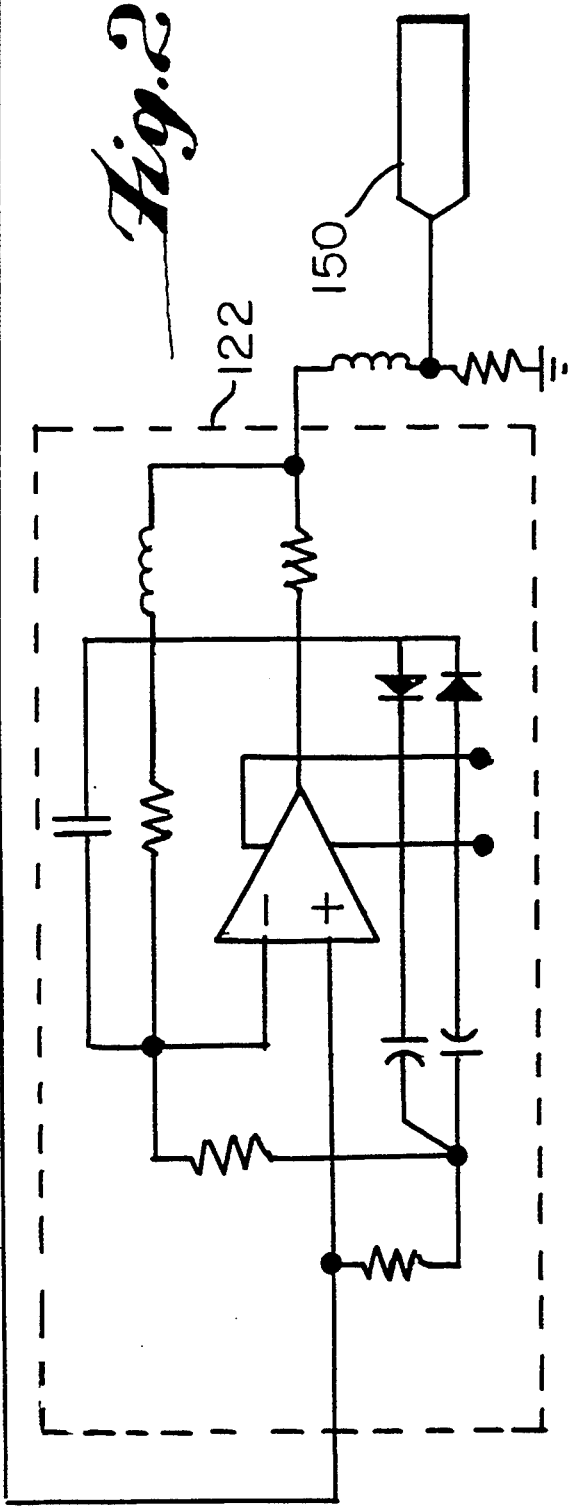

FIG. 26 depicts the circuit diagram for a superposition technique which creates a confusion field to bioprotect an entire living area. The modulation generator 116 implemented in this embodiment generates a random noise signal. This signal is then passed through the low pass filter 118, pre-amplifier 120 and power amplifier 122. The confusion field source which is driven is a coil structure 150.

The range of protection of the home bioprotection system device depends on the magnitude of the current passing through the coil and the radius of the coil. The induced confusion field within the area circumscribed by the coil at the plane of the coil is relatively uniform. The confusion field decreases with distance along the coil axis, however, the attenuation is not significant within a distance of the order of ½ the coil radius. Therefore the protected area includes a cylindrical region circumscribing the coil and extending a distance approximately equal to ½ the coil radius above and below the plane of the coil. For a given current rating and number of turns of the coil the confusion field at the plane of the coil increases with decreasing radius. Therefore for larger areas a larger current rating is required to maintain a confusion field with adequate amplitude to afford bioprotection of the entire area. In general, the device should be designed to produce a confusion field suitable for the "average" regularly oscillating detrimental field measured within an area to be protected. A confusion field of 1 $\mu$T is suitable in most situations. The detrimental field emissions in the proximity of devices with motors can be much larger, but they generally drop off quickly away from the source. When the time of exposure in the proximity of a detrimental field source is large, a device affording localized protection would be more suitable, e.g. the bioprotected keyboard, the bioprotected hair dryer, and the converter box unit.

POWER DISTRIBUTION LINE BIOPROTECTION SCHEME EMBODIMENT

In a multi-user system, electric power from a central station is delivered to each user via a network of distribution lines. Such a network might consist of a series of primary trunks from which secondary lines branch out in successive steps to the final distribution points. The flow of current through each branch of the network depends on the power demands of all users drawing current from that branch. It is easy to see that in large power distribution systems the primary trunks must be capable of handling very large power requirements. The voltage and the current in these power transmission lines are the source of large electric and magnetic fields. Since the voltage is referenced to ground level, the line voltage establishes a large electric potential between it and ground. Line voltages of 500 KV and 230 KV are typical for transmission lines leaving a primary distribution station. A 500 KV line is typically hung 42 feet from the ground therefore establishing an electric field of 39 KV/m beneath it. Experimental evidence indicates that electric fields of this order of magnitude can affect biological function [Freed, C. A., McCoy, S. L., Ogden, B. E., Hall, A. S., Lee, J., Hefeneider, S. H., "Exposure of Sheep to Whole Body field Reduces In-Vitro Production of the Immunoregulatory Cytokine Interleukin 1" Abstract Book, BEMS Fifteenth Annual Meeting, 1993].

The flow of current through a power transmission line causes the induction of magnetic fields on planes perpendicular to the direction of current flow. The magnetic field is oriented tangential to circular paths around the conductor. At distances far removed from a single conductor, the magnetic field decreases in proportion to the inverse of the distance. In single phase circuits two transmission lines are required to deliver power, one to carry the current to the load and another one to return the current to the source and complete the circuit. If the two lines were placed immediately next to each other, the magnetic field from the transmission line pair would tend to cancel because induced by currents of equal magnitude but opposite direction. In practice transmission lines with high voltages must be separated by a minimum distance to prevent dielectric breakdown of the air between the conductors. Consequently, the magnetic fields do not cancel. For example, in the case of 50 KV lines which are typically positioned 30 ft. apart, the magnetic field at the edge of the right of way can be of the order of 3 $\mu$T during peak power consumption intervals when the current is of the order of 1000 Amperes. The width of the right of way is usually 150 ft. so that the horizontal distance from the edge to the nearest conductor is 60 ft. Residences located at the edge of the right of way can be exposed to relatively high magnetic fields. Experimental evidence previously referred to shows that magnetic fields as low as 0.5 $\mu$T can cause bioeffects.

Figure 27:
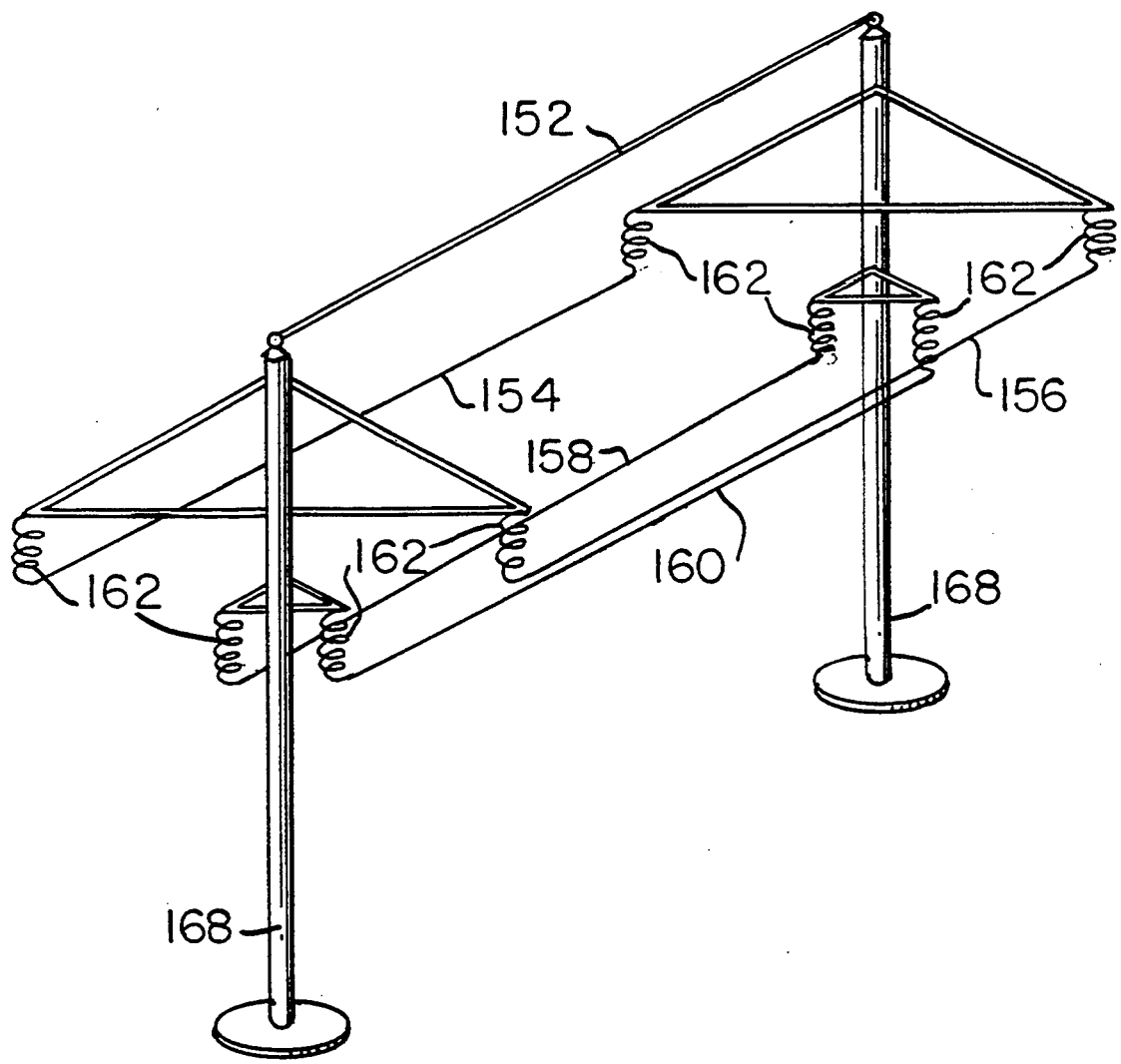
FIG. 27 shows an embodiment of the invention implementing the superposition technique to create a confusion field in the area surrounding a power distribution line.

The magnetic fields from transmission lines can be rendered harmless by superimposing a bioprotection field. In one embodiment of this invention, the bioprotection fields can be induced by current passing through one or two additional conductors running parallel to the transmission line conductors. The bioprotection current must be such that the magnitude of the induced bioprotection magnetic field is equal to or larger than that from the transmission lines. This can be achieved for example with a line frequency signal (e.g. 60 Hz) which is turned on for 0.1 seconds in subsequent one second intervals. The modulation would be imposed at the power station or substations using a low voltage current source. The power consumption of the bioprotection field is limited by the fact that this field is on only ten percent of the time as well as by a lower voltage rating for this line relative to the main high voltage transmission line. Assuming that a current equivalent to that flowing in the transmission line is required to produce the bioprotection field, and a 100 V line is used for the protection circuit for a 500 KV line, the power consumption of the bioprotection circuit would be fifty thousand times lower than that of the main transmission line. FIG. 27 shows one implementation of the superposition technique to create a confusion field in the area surrounding a power distribution line.

Referring to FIG. 27, a power distribution line 154, 156 is strung overground, through the use of electrical insulators 162 supported by poles 168. A static wire 152 is seen as a protection from lightning. The confusion field is generated by the bioprotection wires 158 and 160, which form a single loop coil structure. The bioprotection wires 158 and 160 are also hung from insulators 162. The bioprotection wires 158 and 160 are hung below the static wire 152.

I claim:

1. An apparatus for creating a bioprotective electromagnetic field comprising the combination of:
    an electrical coil for generating an electromagnetic field; and
    an electrical power conversion device, having an input and an output, for modulating within time intervals of less than 10 seconds one or more fundamental properties of an electrical power source when said electrical power source is applied to said input, said fundamental properties including amplitude, period, phase, waveform and polarity, said output of said electrical power conversion device being coupled to said coil for driving said coil, whereby said coil generates a bioprotective electromagnetic field.

2. An apparatus according to claim 1 wherein said time intervals are random intervals, the largest of which is less than 10 seconds.

3. An apparatus according to claim 1 wherein said time intervals are 0.1 to 1 second.

4. An apparatus as recited in claim 1, wherein said electrical power conversion device modulates the amplitude of the electrical power source.

5. An apparatus as recited in claim 1, wherein said electrical power conversion device modulates the period of the electrical power source.

6. An apparatus as recited in claim 1, wherein said electrical power conversion device modulates the waveform of the electrical power source.

7. An apparatus as recited in claim 1, wherein said electrical power conversion device modulates polarity of the electrical power source.

8. An apparatus for creating a bioprotective electromagnetic field in a hair dryer comprising the combination of:
a hair dryer having a heating coil;
an electrical coil for producing an electromagnetic field, said coil being shaped and positioned so that it surrounds said heating coil of said hair dryer; and
an electrical power conversion device, having an input and having an output coupled to drive said coil, for changing within time intervals of less than 10 seconds one or more fundamental properties of an electrical power source when said electrical power source is applied to said input of said electrical power conversion device, said fundamental properties including amplitude, period, phase, waveform and polarity; whereby a bioprotective electromagnetic field is produced from said coil.

9. An apparatus according to claim 8 wherein said time intervals are random intervals, the largest of which is less than 10 seconds.

10. An apparatus according to claim 8 wherein said time intervals are 0.1 to 1 second.

11. An apparatus as in claim 8, wherein said heating coil and said electrical coil are arranged so as to be parallel and have current flowing in opposite directions, respectively.

12. An apparatus as in claim 8, wherein said hair dryer further comprises a sensing device for sensing the bioprotective field.

13. An apparatus for creating a bioprotective electromagnetic field for a computer comprising the combination of:
a computer having a keyboard;
an electrical coil for generating an electromagnetic field, said coil being positioned inside said keyboard of said computer; and
an electrical power conversion device, having an input and an output coupled to said coil, for modulating within time intervals of less than 10 seconds one or more fundamental properties of an electrical power source when said electrical power source is applied to said input, said fundamental properties including amplitude, period, phase, waveform and polarity, said output of said electrical power conversion device driving said coil, whereby said coil generates a bioprotective electromagnetic field.

14. An apparatus according to claim 13 wherein said time intervals are random intervals, the largest of which is less than 10 seconds.

15. An apparatus according to claim 13 wherein said time intervals are 0.1 to 1 second.

16. An apparatus as in claim 13, wherein said electrical power source is contained within said computer.

17. An apparatus as in claim 13, further comprising a sensing device for sensing the bioprotective field.

18. An apparatus for creating a bioprotective electromagnetic field in a space occupied by humans or animals comprising the combination of:
a space to be protected;
an electrical coil for generating an electromagnetic field, said coil being positioned adjacent a wall in said space; and
an electrical power conversion device, having an input and an output coupled to drive said coil, for modulating within time intervals of less than 10 seconds one or more fundamental properties of an electrical power source when said electrical power source is applied to said input, said fundamental properties including amplitude, period, phase, waveform and polarity, whereby said coil generates a bioprotective electromagnetic field.

19. An apparatus according to claim 18 wherein said time intervals are random intervals, the largest of which is less than 10 seconds.

20. An apparatus according to claim 18 wherein said time intervals are 0.1 to 1 second.

21. An apparatus as in claim 18, further comprising a sensing device for sensing the bioprotective field.

22. An apparatus for creating a bioprotective electromagnetic field surrounding a building comprising the combination of:
a building;
an electrical coil for generating an electromagnetic field, said coil surrounding said building; and
an electrical power conversion device, having an input and an output coupled to said coil, for modulating within time intervals of less than 10 seconds one or more fundamental properties of an electrical power source when said electrical power source is applied to said input, said fundamental properties including amplitude, period, phase, waveform and polarity, said output of said electrical power conversion device driving said coil, whereby said coil generates a bioprotective electromagnetic field.

23. An apparatus according to claim 22 wherein said time intervals are random intervals, the largest of which is less than 10 seconds.

24. An apparatus according to claim 22 wherein said time intervals are 0.1 to 1 second.

25. An apparatus as in claim 22, further comprising a sensing device for sensing the bioprotective field.

26. An apparatus for creating a bioprotective electromagnetic field surrounding a cathode ray tube comprising the combination of:
a cathode ray tube having a screen;
an electrical coil for generating an electromagnetic field, said coil surrounding said screen of said cathode ray tube; and
an electrical power conversion device, having an input and an output coupled to said coil, for modulating within time intervals of less than 10 seconds one or more fundamental properties of an electrical power source when said electrical power source is applied to said input, said fundamental properties including amplitude, period, phase, waveform and polarity, said output of said electrical power conversion device driving said coil, whereby said coil generates a bioprotective electromagnetic field.

27. An apparatus according to claim 26 wherein said time intervals are random intervals, the largest of which is less than 10 seconds.

28. An apparatus according to claim 26 wherein said time intervals are 0.1 to 1 second.

29. An apparatus for creating a bioprotective electromagnetic field surrounding a microwave oven comprising the combination of:
   a microwave oven having an outer surface;
   an electrical coil for generating an electromagnetic field, said coil positioned adjacent to an outer surface of said microwave oven; and
   an electrical power conversion device, having an input and an output coupled to said coil, for modulating within time intervals of less than 10 seconds one or more fundamental property of an electrical power source when said electrical power source is applied to said input, said fundamental properties including amplitude, period, phase, waveform and polarity, said output of said electrical power conversion device driving said coil, whereby said coil generates a bioprotective electromagnetic field.

30. An apparatus according to claim 29 wherein said time intervals are random intervals, the largest of which is less than 10 seconds.

31. An apparatus according to claim 29 wherein said time intervals are 0.1 to 1 second.

32. An apparatus for creating a bioprotective electromagnetic field surrounding a mattress comprising the combination of:
   a mattress, having an inside;
   an electrical coil for generating an electromagnetic field, said coil being substantially the size of said mattress, said coil positioned in the inside of said mattress; and
   an electrical power conversion device, having an input and an output coupled to said coil, for modulating within time intervals of less than 10 seconds one or more fundamental properties of an electrical power source when said electrical power source is applied to said input, said fundamental properties including amplitude, period, phase, waveform and polarity, said output of said electrical power conversion device driving said coil, whereby said coil generates a bioprotective electromagnetic field.

33. An apparatus according to claim 32 wherein said time intervals are random intervals, the largest of which is less than 10 seconds.

34. An apparatus according to claim 32 wherein said time intervals are 0.1 to 1 second.

35. An apparatus for creating a bioprotective electromagnetic field in an electrical circuit comprising the combination of:
   an electrical circuit;
   a modulation device having an electrical input and an electrical output;
   a modulation device driver coupled to said modulation device for electrically driving said modulation device; and
   a modulation generator coupled to said driver which controls said modulation device driver within time intervals of less than 10 seconds, said time intervals of control of said modulation device driver altering at least one fundamental property of an electrical source applied to said electrical input of said modulation device, said fundamental property being any of amplitude, period, phase, waveform and polarity, said altered electrical source being available at said output of said modulation device, the use of said apparatus in said electrical circuit generating an electromagnetic field which is modulated at said time intervals.

36. An apparatus according to claim 35 wherein said time intervals are random intervals, the largest of which is less than 10 seconds.

37. An apparatus according to claim 35 wherein said time intervals are 0.1 to 1 second.

38. An apparatus as in claim 35, wherein said electrical output of said modulation device is grounded.

39. An apparatus as in claim 35, wherein said apparatus includes a thermostat.

40. An apparatus as in claim 35, wherein said apparatus includes a hair dryer.

41. An apparatus for converting standard household electrical power into a bioprotective power source comprising the combination of:
   an electrical circuit for conveying electrical power;
   a modulation device having an electrical power source and an electrical power output;
   a modulation device driver coupled to said modulation device for electrically driving said modulation device; and
   a modulation generator means coupled to said driver which controls said modulation device driver within time intervals of less than 10 seconds, said time intervals of control of said modulation device driver altering at least one fundamental property of said electrical power source of said modulation device, said fundamental property being any of amplitude, period, phase, waveform and polarity, said altered electrical power source of said modulation device being applied to said electrical power outlet of said modulation device, the use of said apparatus in said electrical circuit generating an electromagnetic field which is modulated at said time intervals.

42. An apparatus according to claim 41 wherein said time intervals are random intervals, the largest of which is less than 10 seconds.

43. An apparatus according to claim 41 wherein said time intervals are 0.1 to 1 second.

44. An apparatus for creating a bioprotective electromagnetic field in an electrical circuit comprising the combination of:
   an electrical circuit;
   a modulating resistance connected in said circuit; and
   a modulation control device for changing said modulating resistance into different resistances, said changing into different resistances occurring within time intervals of less than 10 seconds, wherein a bioprotective electromagnetic field emanates from said electrical circuit.

45. An apparatus according to claim 44 wherein said time intervals are random intervals, the largest of which is less than 10 seconds.

46. An apparatus according to claim 44 wherein said time intervals are 0.1 to 1 second.

47. An apparatus as in claim 44, wherein said apparatus includes an electric blanket in which said electrical circuit is placed.

48. An apparatus for creating a bioprotective electromagnetic field comprising the combination of:
   an electrical wire for producing an electromagnetic field; and
   an electrical power conversion device, having an input and an output coupled to said wire, for modulating within time intervals of less than 10 seconds one or more fundamental properties of an electrical power source when said electrical power source is applied to said input of said electrical power conversion means, said fundamental properties including amplitude, period, phase, waveform and polarity, whereby said wire produces a bioprotective electromagnetic field.

49. An apparatus according to claim 48 wherein said time intervals are random intervals, the largest of which is less than 10 seconds.

50. An apparatus according to claim 48 wherein said time intervals are 0.1 to 1 second.

51. An apparatus for bioprotecting a power transmission line comprising the combination of:
a power transmission line;
a non-power carrying conductor placed so as to be parallel to said power transmission line; and
current generating apparatus coupled to said conductor for causing a current to flow in said conductor, the current being such that a magnetic field induced thereby is equal to or larger than that from said transmission line.

52. An apparatus according to claim 51 wherein said current causing means comprises means for causing current to flow that is turned on for 0.1 seconds in one second intervals.

* * * * *